(12) United States Patent
Majumdar et al.

(10) Patent No.: US 10,984,888 B2
(45) Date of Patent: Apr. 20, 2021

(54) METHODS AND SYSTEMS FOR A DIGITAL PCR EXPERIMENT DESIGNER

(71) Applicant: LIFE TECHNOLOGIES CORPORATION, Carlsbad, CA (US)

(72) Inventors: Nivedita Sumi Majumdar, Foster City, CA (US); Thomas Wessel, Pleasanton, CA (US); David C. Woo, Foster City, CA (US); Marcin Sikora, Burlingame, CA (US); Gordon A. Janaway, Castro Valley, CA (US); Shweta Raizada, Southfield, MI (US); Joanna Lankester, San Carlos, CA (US); Jeffrey A. Marks, Mountain View, CA (US); Daniel Wessel, Pleasanton, CA (US)

(73) Assignee: Life Technologies Corporation, Carlsbad, CA (US)

( * ) Notice: Subject to any disclaimer, the term of this patent is extended or adjusted under 35 U.S.C. 154(b) by 1017 days.

(21) Appl. No.: 14/428,312

(22) PCT Filed: Sep. 13, 2013

(86) PCT No.: PCT/US2013/059815
§ 371 (c)(1),
(2) Date: Mar. 13, 2015

(87) PCT Pub. No.: WO2014/043581
PCT Pub. Date: Mar. 20, 2014

(65) Prior Publication Data
US 2015/0278437 A1    Oct. 1, 2015

Related U.S. Application Data

(60) Provisional application No. 61/830,507, filed on Jun. 3, 2013, provisional application No. 61/788,272, filed on Mar. 15, 2013, provisional application No. 61/758,216, filed on Jan. 29, 2013, provisional application No. 61/714,137, filed on Oct. 15, 2012, provisional application No. 61/701,380, filed on Sep. 14, 2012.

(51) Int. Cl.
*G16B 25/00*    (2019.01)
*G16B 40/00*    (2019.01)
*C12Q 1/686*    (2018.01)

(52) U.S. Cl.
CPC .............. *G16B 25/00* (2019.02); *C12Q 1/686* (2013.01); *G16B 40/00* (2019.02)

(58) Field of Classification Search
None
See application file for complete search history.

(56) References Cited

U.S. PATENT DOCUMENTS

2009/0239308 A1    9/2009 Dube et al.

FOREIGN PATENT DOCUMENTS

WO    2010/018465 A2    2/2010

OTHER PUBLICATIONS

Applied Biosystems, "Applied Biosystems StepOne and StepOnePlus Real-Time PCR Systems for Genotyping Experiments", *Getting Started Guide*, Jun. 2010, 1-156.
Dube, Simant et al., "Mathematical Analysis of Copy Number Variation in a DNA Sample Using Digital PCR on a Nanofluidic Device", *PLoS One*, vol. 3, No. 8, Aug. 2008, e2876.
Kreutz, Jason et al., "Theoretical Design and Analysis of Multivolume Digital Assays Wide Dynamic Range Validated Experimentally with Microfluidic Digital PCR", *Analystical Chemistry, American Chemical Society*, vol. 83, No. 21, Oct. 7, 2011, 8158-8168.
The Statistics of Measurements, "The Statistics of Measurements: Chapter 3: Measurements as Random Variables", Jan. 2000, 53-80.
Whale, Alexandra S. et al., "Comparison of Microfluidic Digital PCR and Conventional Quantitative PCR for Measuring Copy Number Variation", *Nucleic Acids Research*, vol. 40, No. 11, e82, 2012, 1-9.
"OpenArray Real-Time PCR System—Digital PCR Experiments User Guide", http://tools.thermofisher.com/content/sfs/manuals/cms_088717, Oct. 2010.

*Primary Examiner* — Joseph Woitach
(74) *Attorney, Agent, or Firm* — Life Technologies Corporation

(57) ABSTRACT

A computer-implemented method for designing a digital PCR (dPCR) experiment is provided. The method includes receiving, from a user, a selection of optimization type. The optimization type may be maximizing the dynamic range, minimizing the number of substrates including reaction sites needed for the experiment, determining a dilution factor, or determining the lower limit of detection, for example. The method further includes receiving, from the user, a precision measure for an experiment, and a minimum concentration of a target in a reaction site for the experiment. The method also includes determining a set of dPCR experiment design factors for the experiment based on the optimization type. The set of dPCR experiment design factors is then displayed to the user.

19 Claims, 41 Drawing Sheets dPCR Experiment Setup Calculator

A tool for doing the calculations necessary to design a dPCR experiment using what information is available about the consumable, the system in use, the sample, and targets of interest.

1 Pick the problem you are trying to solve

○ Rare Mutation  ◉ Optimize detection attributes of your digital experiment for Absolute Quantification  ○ Use qPCR or NanoDrop data to estimate dilution factor for your digital experiment.

Consider putting some sort of verbage here to explain their choice?

2 Select what you'd like to do

◉ Maximize dynamic range  ○ Minimize number of chips  ○ Calculate Dilution Factor  ○ Calculate lower limit of detection How do you want to constrain this? [Precision ▸]   Show Advanced Inputs

Standard Inputs

Precision: [10] [% ▸]   Describes how close two quantities can be and still be distinguished by the system, at a certain confidence level. It is calculated as the ratio of the spread of the confidence interval around the copies/rxn compared to the true value of the copies/rxn.

Minimum copies/rxn: [0.01] [copies/rxn ▸]   The minimum readable concentration, anything lower will be ignored.

[ Optimize ]

Help make this product better! Send your comments about this page, or the product overall.   Life Technologies

FIG. 21A

3 Get Results

Results Summary

Results reached using 1 chip on first dilution and 1 chip on second dilution Single Dilution Dynamic Range: [2.571] In Log10 units Single Dilution Range of Detection min/max: [0.021] [7.958] In copies/rxn Multiple Dilutions Dynamic Range: [4.872] In Log10 units Multiple Dilution Range of Detection min/max: [0.021] [1591.515] In copies/rxn Dilution Factor: [0.005]

[Show me my stock mix]

---

Results Graph (HIDDEN)                                    Show Graphs

Stock Concentration Inputs                          Show Advanced Inputs

What type of experiment are you running?
[SINGLEPLEX ▼]

Desired volume of dPCR mix:          Smallest Sample Pipette Volume:
[20] [uL ▼]                          [1 uL]

[Calculate]

*FIG. 21C*

Results reached using 1 chip on first dilution and 1 chip on second dilution Single Dilution Dynamic Range: 2.571
In Log10 units Single Dilution Range of Detection min/max: 0.021 | 7.958
In copies/rxn Multiple Dilutions Dynamic Range: 4.872
In Log10 units Multiple Dilution Range of Detection min/max: 0.021 | 1591.515
In copies/rxn Dilution Factor: 0.005

[Show me my stock mix]

Stock Concentration Inputs                    Show Advanced Inputs

What type of experiment are you running?: SINGLEPLEX ▼

Desired volume of dPCR mix: 20 uL ▼

Smallest Sample Pipette Volume: 1 uL ▼

[Calculate]

Stock Solution Set-up Dilution 1

| Item | Final Concentration in Reaction Mix | Volume |
|---|---|---|
| 2x Master Mix | 1x | 10 |
| 20x FAM Assay | 1x | 1 |
| Sample | 0.45x | 9 |
| Water | 1x | 0 |
| Total Volume | | 20 |

Stock Solution Set-up Dilution 2

Initial Sample Dilution (apart from reaction mix): 0.005
Dilution Factor: 1/10, 1/10, 1/2
Equivalent Dilution Series:
*Dilute Sample by this amount before creating final mix

| Item | Final Concentration in Reaction Mix | Volume |
|---|---|---|
| 2x Master Mix | 1x | 10 |
| 20x FAM Assay | 1x | 1 |
| Sample | 0.00225x | 9 |
| Water | 1x | 0 |
| Total Volume | | 20 |

*FIG. 21D* dPCR Experiment Setup Calculator

A tool for doing the calculations necessary to design a dPCR experiment using what information is available about the consumable, the system in use, the sample, and targets of interest.

1 Pick the problem you are trying to solve

⊙ Rare Mutation   ○ Optimize detection attributes of your digital experiment for Absolute Quantification   ○ Use qPCR or NanoDrop data to estimate dilution factor for your digital experiment.

Consider putting some sort of verbage here to explain their choice?

2 We need information on your stock solution. Please select what data you have.

⊙ NanoDrop Concentration   ○ Single CT   ○ Multiple CT (Swillens)

What information do you know about the genome?  [Select ▸]

How do you want to constrain the Lower Limit of Detection?  [Select ▸]

Help make this product better! Send your comments about this page, or the product overall.

Life Technologies

FIG. 22A

2 We need information on your stock solution. Please select what data you have.

⦿ NanoDrop Concentration   ○ Single CT   ○ Multiple CT (Swillens)

What information do you know about the genome? | I know my Diploid Genome Weight ▸

How do you want to constrain the Lower Limit of Detection? | I know the False Positive Distribution ▸

Dilution Factor Inputs                                                                 Show Advanced Inputs
Diploid Genome Weight:
| 3.3 | pg ▸ |   The weight of the Diploid Genome.
Sample Concentration:
| 50 | ng/ul ▸ |   The concentration from the NanoDrop reading.

Standard Inputs                                                                        Show Advanced Inputs
Fold Change Desired:
| 0.01 | rare/wild ▸ |   The desired fold change from rare to wild that you are expecting to detect.
P-Value:
| 0.025 | Decimal ▸ |
False Positive distribution Mean:
| 10 | Positive/chip ▸ |      The False Positive distribution can be found by running Non Template Control (NTC)
False Positive distribution Standard Deviation:       1. Mean
| 2 | Positives/chip ▸ |      2. Standard Deviation
                              3. P-value: Probability that result belongs to False Positive distribution

| Solve |

Help make this product better! Send your comments about this page, or the product overall.                Life Technologies

METHODS AND SYSTEMS FOR A DIGITAL PCR EXPERIMENT DESIGNER

BACKGROUND

Digital PCR (dPCR) is an analytical technique that used to provide absolute quantitation of nucleic acid samples, to detect and quantify the concentration of rare targets, and to measure low fold-changes in nucleic acid concentration.

In dPCR, a solution containing a relatively small number of a target polynucleotide or nucleotide sequence may be subdivided into a large number of small test samples, such that each sample generally contains either one or more molecule of the target nucleotide sequence or none of the target nucleotide sequence. When the samples are subsequently thermally cycled in a PCR protocol, procedure, or experiment, the samples containing the target nucleotide sequence are amplified and produce a positive detection signal, while the samples containing no target nucleotide sequence are not amplified and produce no detection signal.

Potentially, a dPCR system may have a very high precision enabling accurate measurement for genetic quantification. The challenge with an unknown sample is to perform the experiment at a dilution that falls within the dynamic range supported by the system.

Generally, increasing the number of replicates increases the accuracy and reproducibility of dPCR results. The dynamic range depends on the total number of available reaction vessels and on the measurement precision necessary for your application.

SUMMARY

In one exemplary embodiment, a computer-implemented method for designing a digital PCR (dPCR) experiment is provided. The method includes receiving, from a user, a selection of optimization type. The optimization type may be maximizing the dynamic range, minimizing the number of substrates including reaction sites needed for the experiment, determining a dilution factor, or determining the lower limit of detection, for example. The method further includes receiving, from the user, a precision measure for an experiment, and a minimum concentration of a target in a reaction site for the experiment. The method also includes determining a set of dPCR experiment design factors for the experiment based on the optimization type. The set of dPCR experiment design factors is then displayed to the user.

DESCRIPTION OF THE FIGURES

FIG. 21A, FIG. 21B, FIG. 21C, FIG. 21D illustrate a method for a gene expression workflow using the dPCR experiment designer according to various embodiments described herein.

Figure 22D:
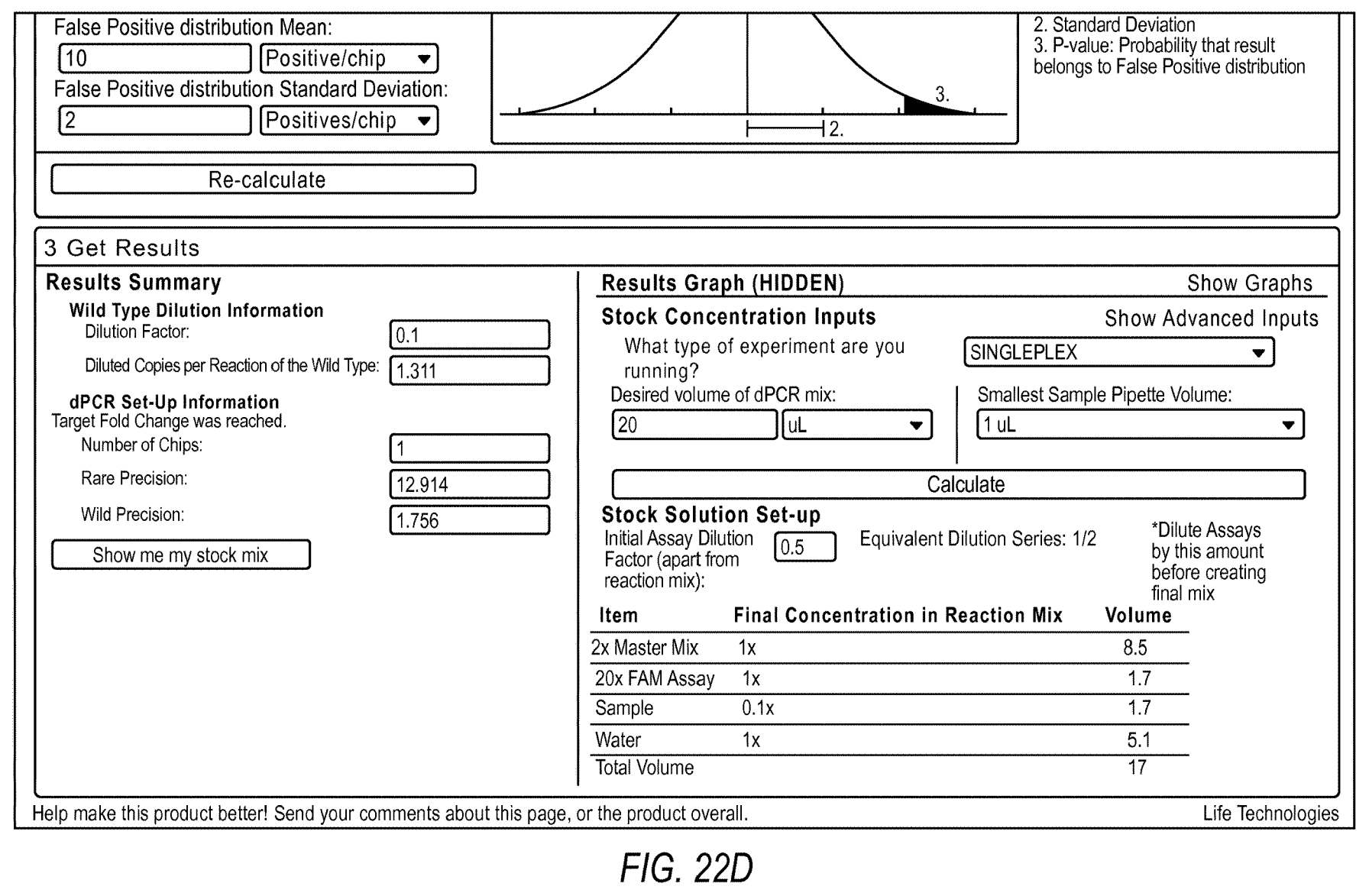

FIG. 22A, FIG. 22B, FIG. 22C, and FIG. 22D illustrate a method within the rare mutation detection workflow using the dPCR experiment designer according to various embodiments described herein.

DETAILED DESCRIPTION

Figure 1A:
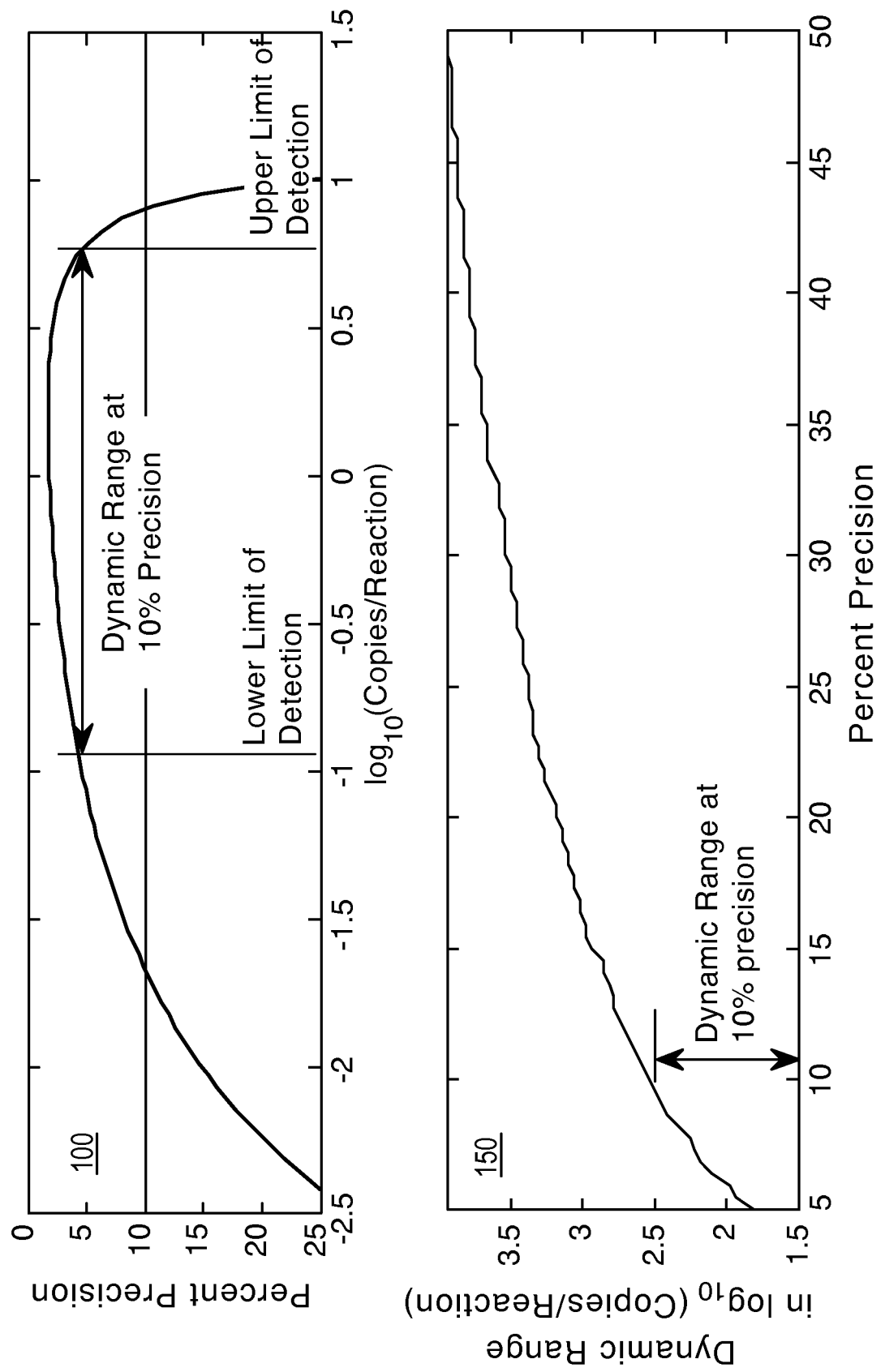
FIG. 1A and FIG. 1B illustrate graphs showing the relationship of dynamic range, measurement precision, and the lower and upper limits of detection according to various embodiments of the present teachings.

Digital PCR Modeling for Maximal Sensitivity, Dynamic Range and Measurement Precision The great promise of digital PCR is the potential for unparalleled precision enabling accurate measurements for genetic quantification. When maximal precision is desired, a challenge with an unknown sample is to perform the experiment at a dilution that supports the detection of one or multiple targets of interest at the required measurement precision. A mathematical framework can be used for modeling a digital PCR system with factors impacting precision such as the number of available reaction sites, sample volume reduction (due to a variety of causes), and false negative/false positive rates. This framework is used to develop graphics showing the relationship between precision and the supported dynamic range. The impact of total input sample volume on the lowest limit of detection or sensitivity is also illustrated. According to various embodiments, this framework may be used in methods encoded on a computer-readable medium implementable on a processor of a computing system as a digital PCR experiment designer.

According to various embodiments, a set of graphics modeling the effects of various system parameters can serve as a powerful tool for users to estimate dilution factors and number of reaction sites necessary to get to a digital answer with the desired precision. The model predicts an increase in supported dynamic range, at a given precision, for the same number of reaction sites with the use of two dilution points (using half the number of reaction sites for each dilution). This increase in dynamic range is obviously advantageous where continuous detection across an entire dynamic range is desirable (e.g., genetic quantification). The loss of half the number of reaction sites to a second dilution point incurs a slight loss in the detectable concentration range at a given precision. However, this loss is more than offset by the gain in the set of detectable concentrations because of an overlapping effect of the second dilution point. The results may also predict possibilities to leverage the available number of reaction sites to enable precise detection of two targets present at largely different proportions within a given sample by careful choice of dilution factors. In some embodiments, a majority of the available reaction sites may be dedicated to detecting the rare type and the remaining sites may be dedicated to detecting the wild type at a very different dilution.

The Digital PCR Model

In a digital PCR experiment, sample DNA is partitioned into a large number of reaction sites so that each gets none or one or more copies. After performing PCR, amplification may be detected in reaction sites that contained a DNA template whereas no amplification may be detected in reaction sites lacking a DNA template.

The reaction sites that do not show an amplified sample are referred to as negatives and reaction sites that show amplification are referred to as positives. Let $\lambda$ denote the average number of molecules per reaction chamber and $p$ denote the fraction of negatives across n reaction sites in a digital PCR experiment. Thus, the fraction of negatives 'p' is related to $\lambda$ by the following equations:

$$p = e^{-\lambda} \quad (1)$$

$$= \frac{r}{n}, \quad (2)$$

where r=number of negative reaction sites; n=total number of reaction sites. The number of substrates including reaction sites in a system is N. Thus, for example, if a substrate includes 20000 reaction sites, then n=20000*N.

Using a large number of reaction sites with the assumption of Poisson distribution of copies, the average number of copies per reaction site can be calculated as $\lambda = -\ln(r/n)$, where r is the number of negative results and n is the total number of reaction sites. Thus, the concentration of target in the input volume may be estimated.

The confidence bounds around the estimate of $\lambda$ are given by equation 3.

$$\text{Confidence Bound}_{(Lower, Upper)} = \exp[\ln(-\ln p) \mp 1.96\sigma], \quad (3)$$

Figure 3:
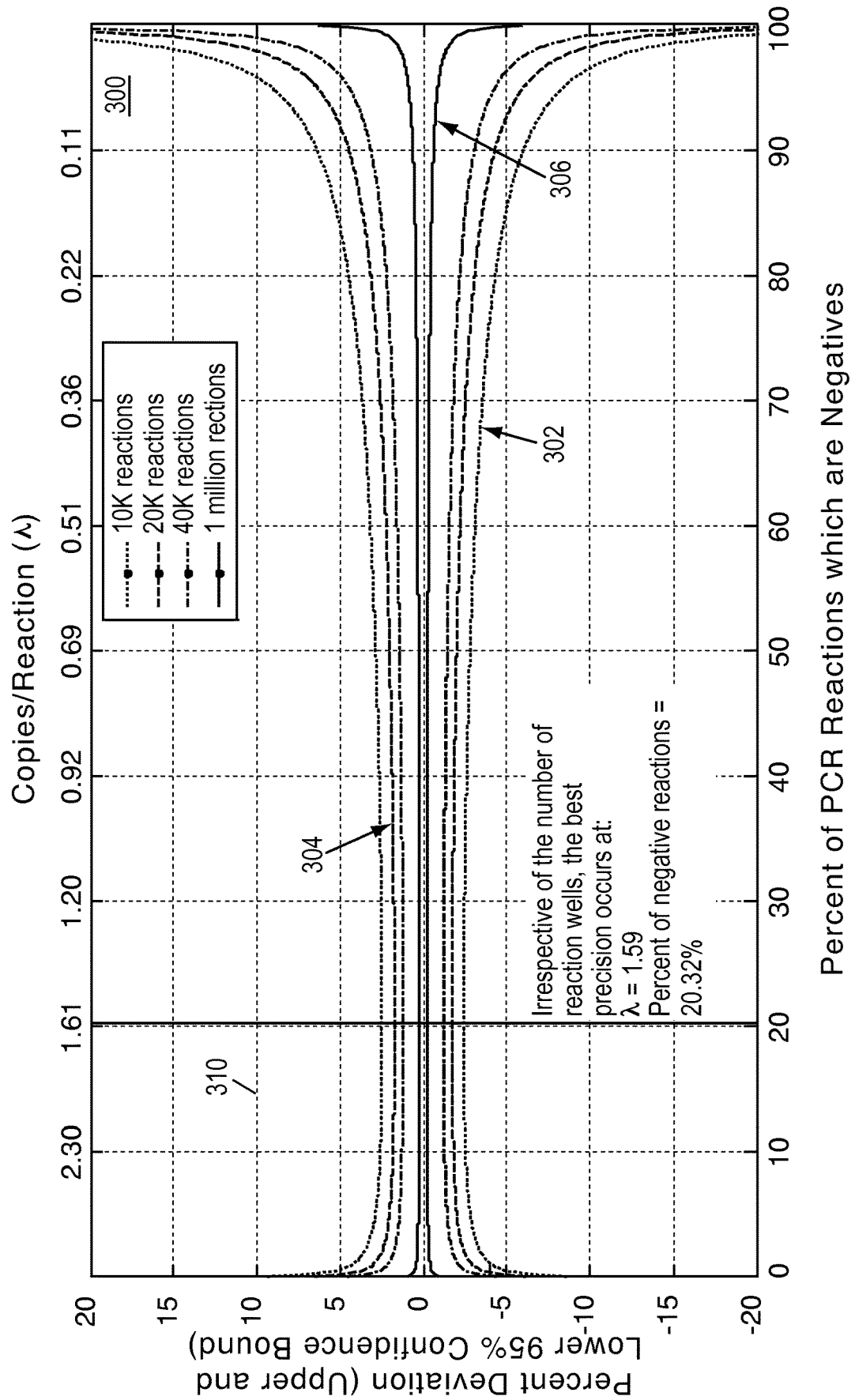
FIG. 3 illustrates a plot showing the optimal concentration ranges for dPCR experiments according to various embodiments described herein.

Precision is defined as the spread of the confidence interval around $\lambda$ compared to the true value of $\lambda$. The smaller this spread, the more precise is the estimate. Precision governs the upper limit of how close two values can be and yet be detectable by the system. The precision measurement is not uniform at all concentrations. FIG. 3 shows a plot 300 showing a confidence interval around the measurement for a range of concentrations (expressed in molecules per reaction) for 10K, 20K, 40K and 1M reaction sites. In this example, the best precision is achieved at a concentration showing 20.32% fraction of negative reactions (irrespective of number of reactions), indicated by marker 310. FIG. 3 also shows that precision deteriorates more rapidly toward the higher concentrations. Plot 302 shows a percent deviation versus the concentration in each reaction site and the percentage of negatives for 10 k reactions. Plot 304 shows a percent deviation versus the concentration in each reaction site and the percentage of negatives for 20 k reactions. Plot 306 shows a percent deviation versus the concentration in each reaction site and the percentage of negatives for 1M reactions. In this example, the drop in precision is sharper as the load concentration increases (right to left on the x axis) than as the load concentration decreases (left to right on the x axis). From this perspective, it may be advisable to err on the side of using more dilute samples for the experiment. The measurement precision for $\lambda$ is given by:

$$\text{Precision} = \frac{1}{\lambda}(\exp[\ln(-\ln p) \mp 1.96\sigma] - \lambda) \quad (4)$$

The variation represented by $\sigma$ in log $\lambda$ space constitutes Poisson or sampling related component as shown in equation 5:

$$\sigma = \sigma_{sampling} = -\frac{\sqrt{1-p}}{(\ln p)\sqrt{np}} \quad (5)$$

Digital PCR results are based on having at least one negative or one positive result. Otherwise, with all negatives or all positives, it is not possible to deduce the concentration of a sample within the reaction volume within a reaction site based on the dPCR theory. The experimental scenario with only one negative or only one positive result gives the limits of detection for a dPCR experiment.

The low limit of detection (LLOD) occurs where there is only one positive. Given that there exists any samples, the probability of getting all negatives can be set to (1−confidence); or equivalently, the probability of getting at least one positive can be set to the confidence level. For example, for a 95% confidence level at the low limit, the presence of the sample should be detected in 95% of experiments, while the other 5% of experiments would show no positives. Solving for the λ at that point gives λ at low limit of detection, or $\lambda_{LLOD}$ given as:

$$\lambda_{LLOD} = -\ln((1-C)^{1/n})) \quad (6)$$

, where C is the confidence level.

The upper Limit of Detection (ULOD) occurs where there is only one negative. The probability of getting all positives can be set to (1−confidence); or equivalently, the probability of getting at least one negative can be set to the confidence level. Solving for the λ at that point gives λ at high limit of detection, $\lambda_{ULOD}$ as:

$$\lambda_{ULOD} = -\ln(1-(1-C)^{1/n}) \quad (7)$$

, where C is the confidence level.

Figure 2:
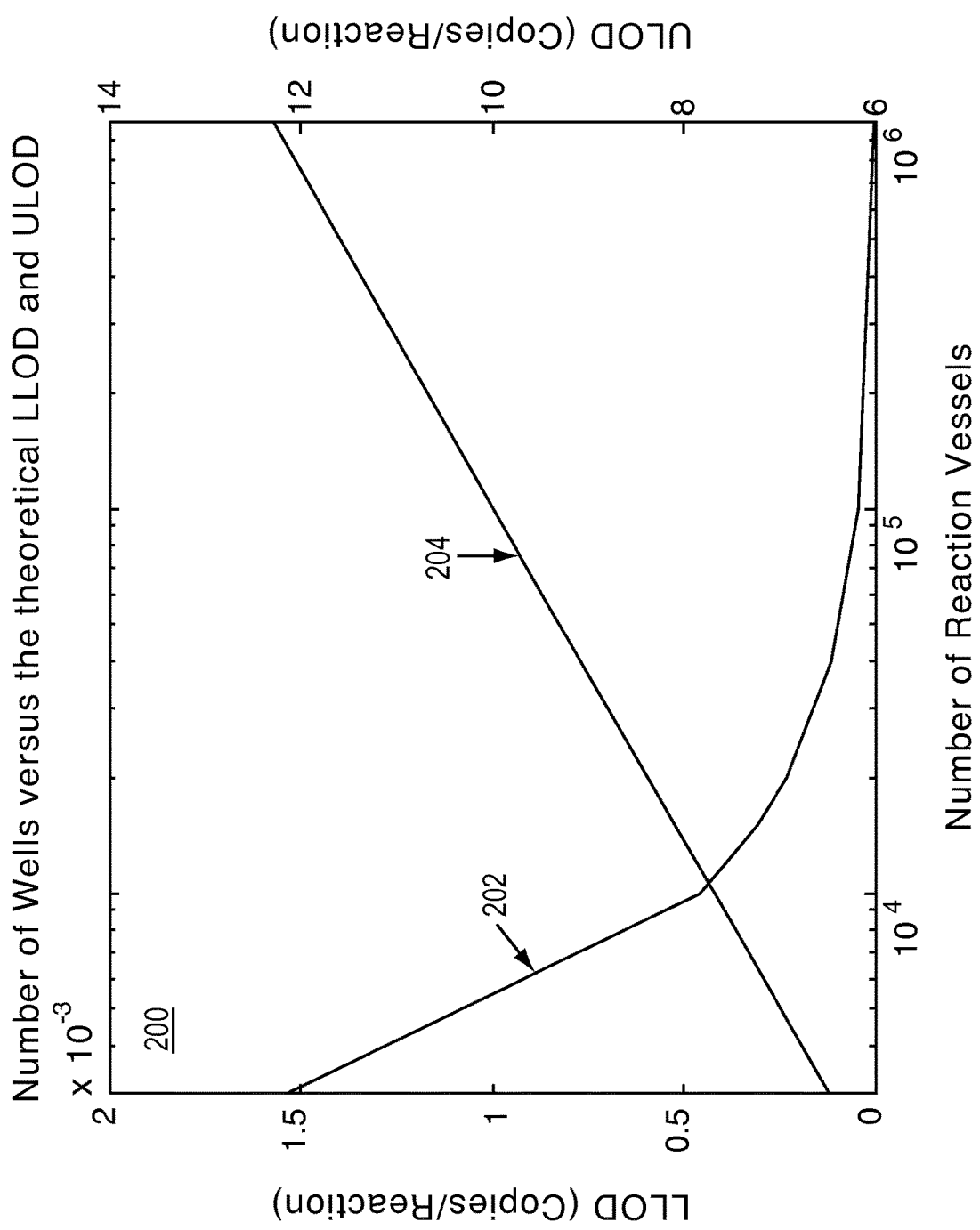
FIG. 2 illustrates a plot showing the relationship of the lower limit of detection (LLOD) and the upper limit of detection (ULOD) to the number of substrates including reaction sites according to various embodiments described herein.

The ULOD and LLOD as defined described the theoretical limits of detection. However, because the measurement precision at the ULOD and LLOD are very poor, one can conceive of defining the limits of detection in terms of a minimum required precision. Alternately, one can choose to define arbitrary limits of detection depending on how many actual positives or negatives one would like to see in an experiment based upon the noise characteristics of the system. The limits of detection can also depend on the number of reaction sites. Plot 202 of graph 200 in FIG. 2 shows how the lower limit of detection is lowered by increasing the number of reaction sites. Plot 204 of graph 200 in FIG. 2 shows how the upper limit of detection is raised by increasing the number of reaction sites.

Figure 1B:
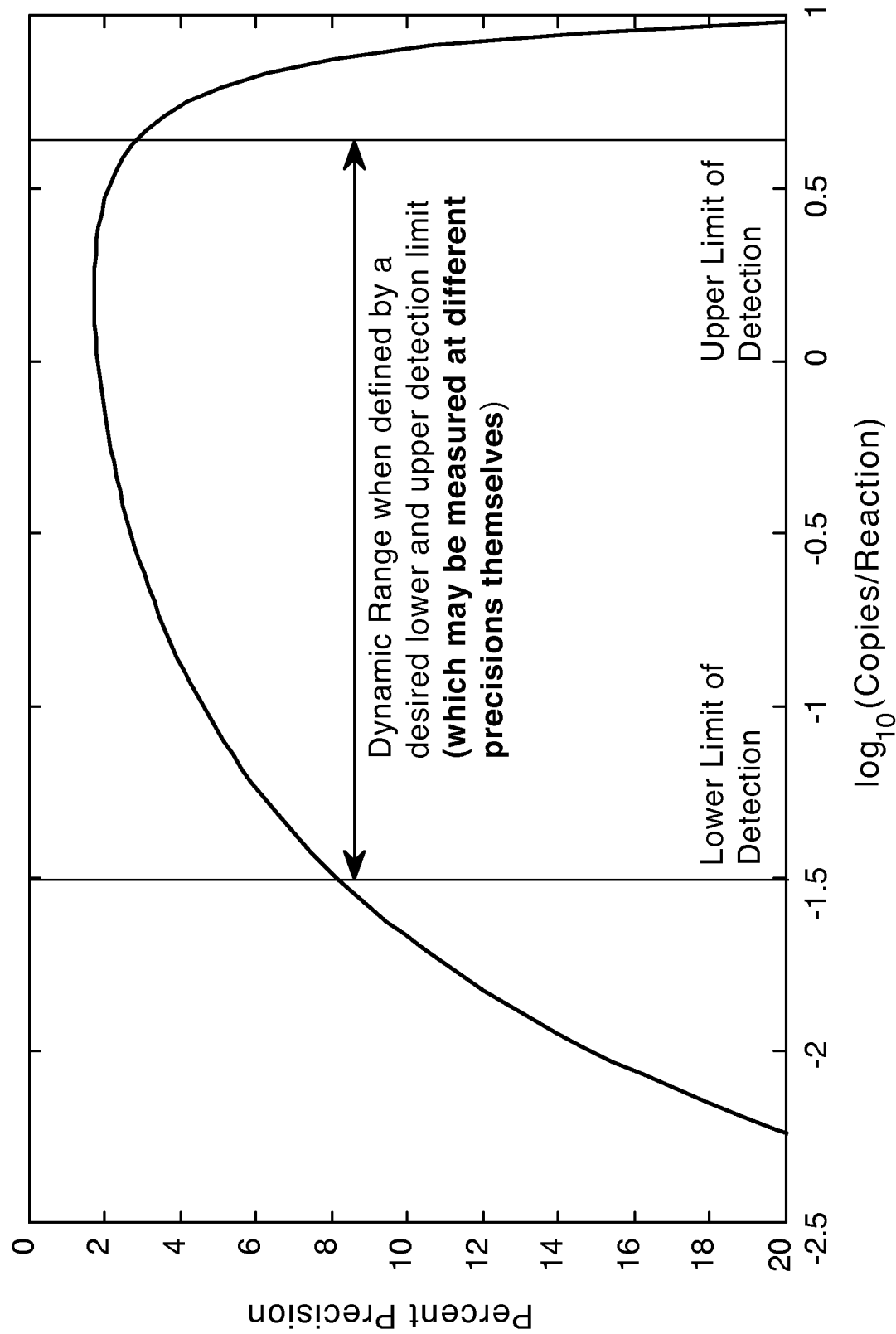

Within this context, the dynamic range defines the span of detectable concentrations in log 10 units. The dynamic range is usually qualified by two other pieces of information: a detection precision and the lowest detectable concentration. Plot 100 in FIG. 1A shows the dynamic range at 10% precision for 20000 reaction sites. Plot 150 in FIG. 1A also shows how the dynamic range increases with lower precision requirement from the system. The dynamic range (DR) may also be constrained by a defining an explicit lower and upper limits for detection as shown in FIG. 1B.

$$DR = \log 10^{\left(\frac{\lambda_{ULOD}}{\lambda_{LLOD}}\right)} \quad (8)$$

Figure 4:
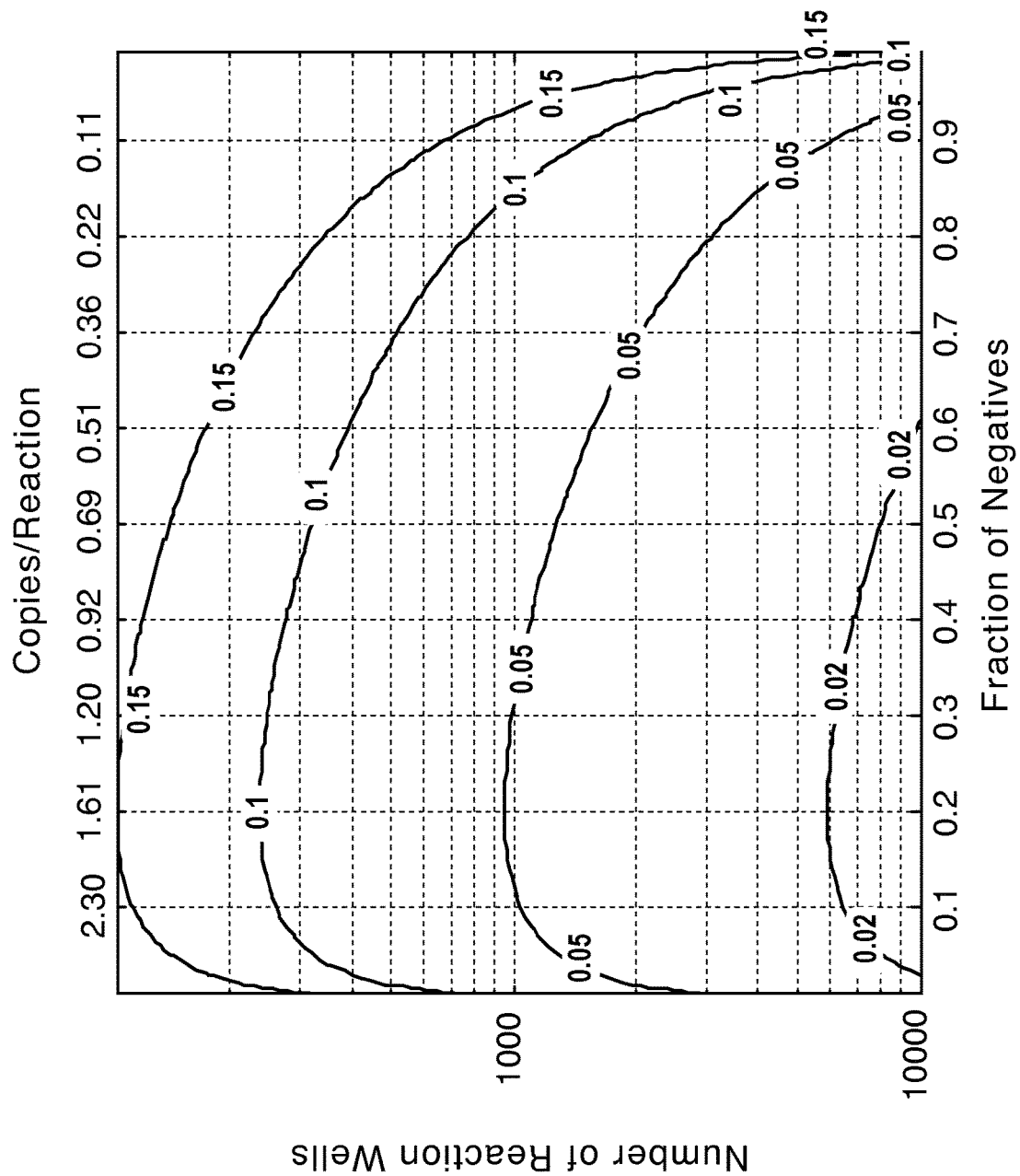
FIG. 4 illustrates a plot showing how precision improves with a larger number of reactions according to various embodiments described herein.
Figure 5:
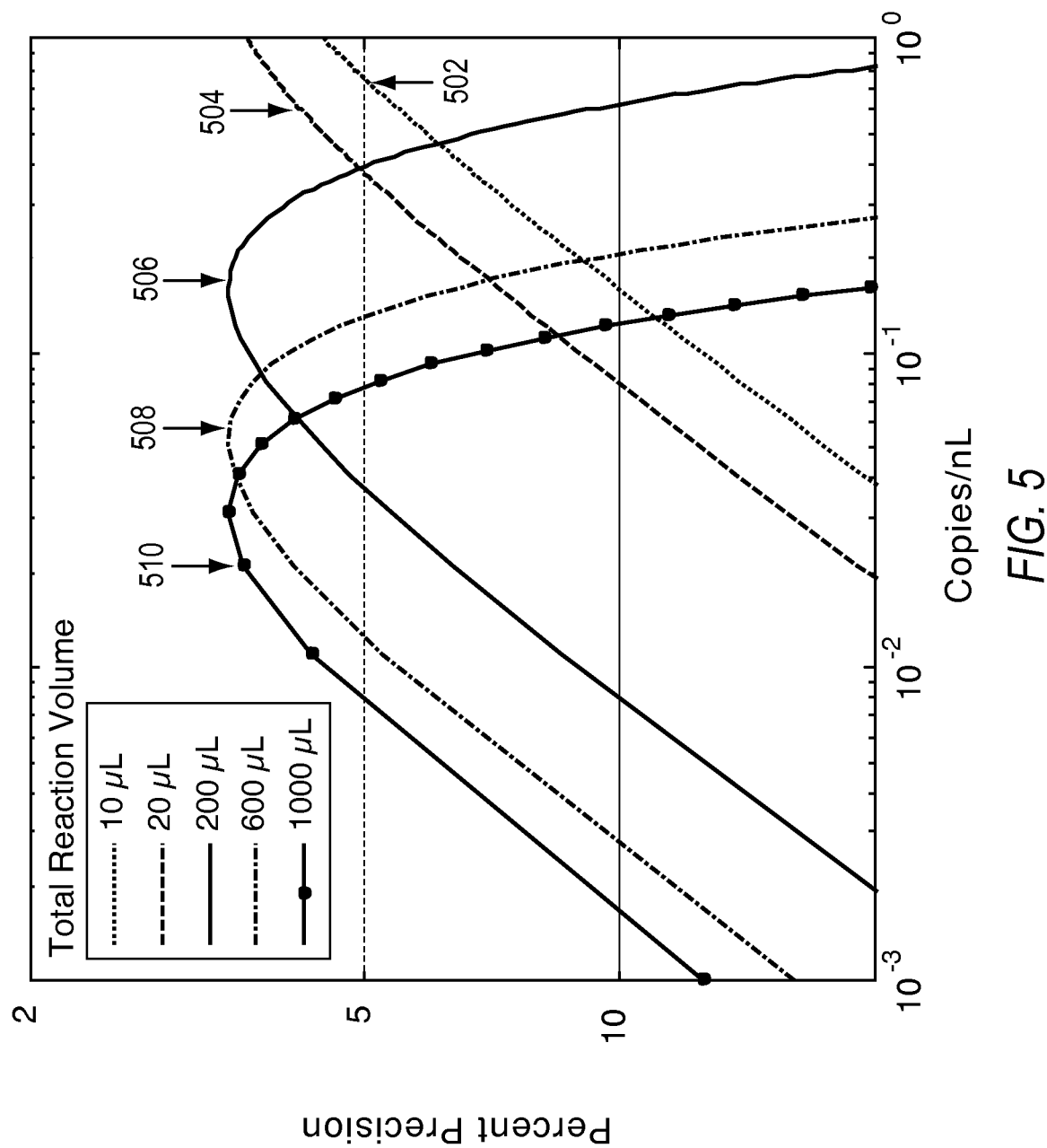
FIG. 5 illustrates the effect of total interrogated volume on the lowest limit of detection according to various embodiments described herein.

The detection precision is mainly influenced by the number of available reaction sites and the lowest detectable concentration is mainly influenced by the total sample volume interrogated. FIG. 3 and FIG. 4 show how precision improves with the larger numbers of reaction vessels. The contours in FIG. 4 are values of measurement precision expressed as a fraction. The precision values become lower (improved) with increased number of reaction sites. FIG. 5 shows how the lowest detectable concentration changes with volume for a fixed number of reaction sites (assuming reaction sites accommodate a larger unit volume); this clarifies that the contributing factor toward improved lower limit of detection is the total sample volume interrogated. For detecting rare event, the focus should thus be toward higher total sample volume than number of reaction sites. The plots generated in FIG. 5 show 20,000 reaction sites, as an example. Plot 502 shows concentration versus precision for a 10 μL reaction volume. Plot 504 shows concentration versus precision for a 20 μL reaction volume. Plot 506 shows concentration versus precision for a 200 μL reaction volume. Plot 508 shows concentration versus precision for a 600 μL reaction volume. Plot 510 shows concentration versus precision for a 1000 μL reaction volume.

Error Modeling

This section introduces noise factors into the pure Poisson model. A reaction site with a target molecule that goes undetected produces a false negative. A reaction site that does not have a target molecule, but gets classified as a positive reaction produces a false positive. Possible causes for false negatives could be an amplification failure, for example. Possible causes for false calls include contamination, chemistry effects, source sample related effects, and optical or system noise effects, for example. As such, a variation component of Equation 5 can be expanded to include variation from two other factors:

False positive, false negative call rate

System related bias

This additional variation is estimated as follows: Let $\lambda_{false}$ denote the λ observed because of the false positive and false negative calls. It is related to the true λ as shown in equation 9.

$$\lambda_{false} = -\ln(e^{-\lambda} - \text{false Positive Rate} + \text{false Negative Rate}) \quad (9)$$

The fraction of negatives observed is given by equation 10.

$$p_{false} = \exp(-\lambda_{false}) \quad (10)$$

Using the fraction of negatives given by (10) in equation (3), the 95% confidence bounds can be found as shown in equation (11):

$$\text{Confidence Bound}_{(Lower,Upper)}^{False} = \exp\left[\ln(-\ln p_{false}) \mp 1.96 \frac{\sqrt{1-p_{false}}}{-(\ln p_{false})\sqrt{np_{false}}}\right]. \quad (11)$$

The variation from sampling and non-zero false positive and false negative call rates is given as:

$$\sigma_{false\ calls, sampling} = \max\left(\frac{\ln(\text{Confidence Bound}_{(Upper,Lower)}^{False}) - \ln(\lambda_{false})}{1.96}\right) \quad (12)$$

An arbitrary source of variation related to system noise, $\sigma_{systemBias}$, is pooled along with above variation, giving the total variation as:

$$\sigma_{total} = \sqrt{\sigma_{falsecalls,sampling}^2 + \sigma_{SystemBias}^2} \quad (13)$$

This leads to an expanded confidence bound given by equation (14).

$$\text{Confidence Bound}_{(Lower,Upper)} = \exp[\ln(-\ln p) \mp 1.96\sigma_{total}] \quad (14)$$

Expression (14) is substituted into the precision formula in equation (4) for a more accurate estimate of precision:

$$\text{Precision} = \frac{1}{\lambda}(\exp[\ln(-\ln p) \mp 1.96\sigma_{total}] - \lambda) \quad (15)$$

The impact from false call rates are investigated using Monte Carlo simulations as follows: Under the influence of zero false call rates, a load concentration yielding 20% negatives affords the best precision. But as the false negative rate increases, it is desirable to target a higher percent negatives for optimal measurement precision. The lower (upper) limit of detection is maximally impacted by false positives (negatives).

Figure 6:
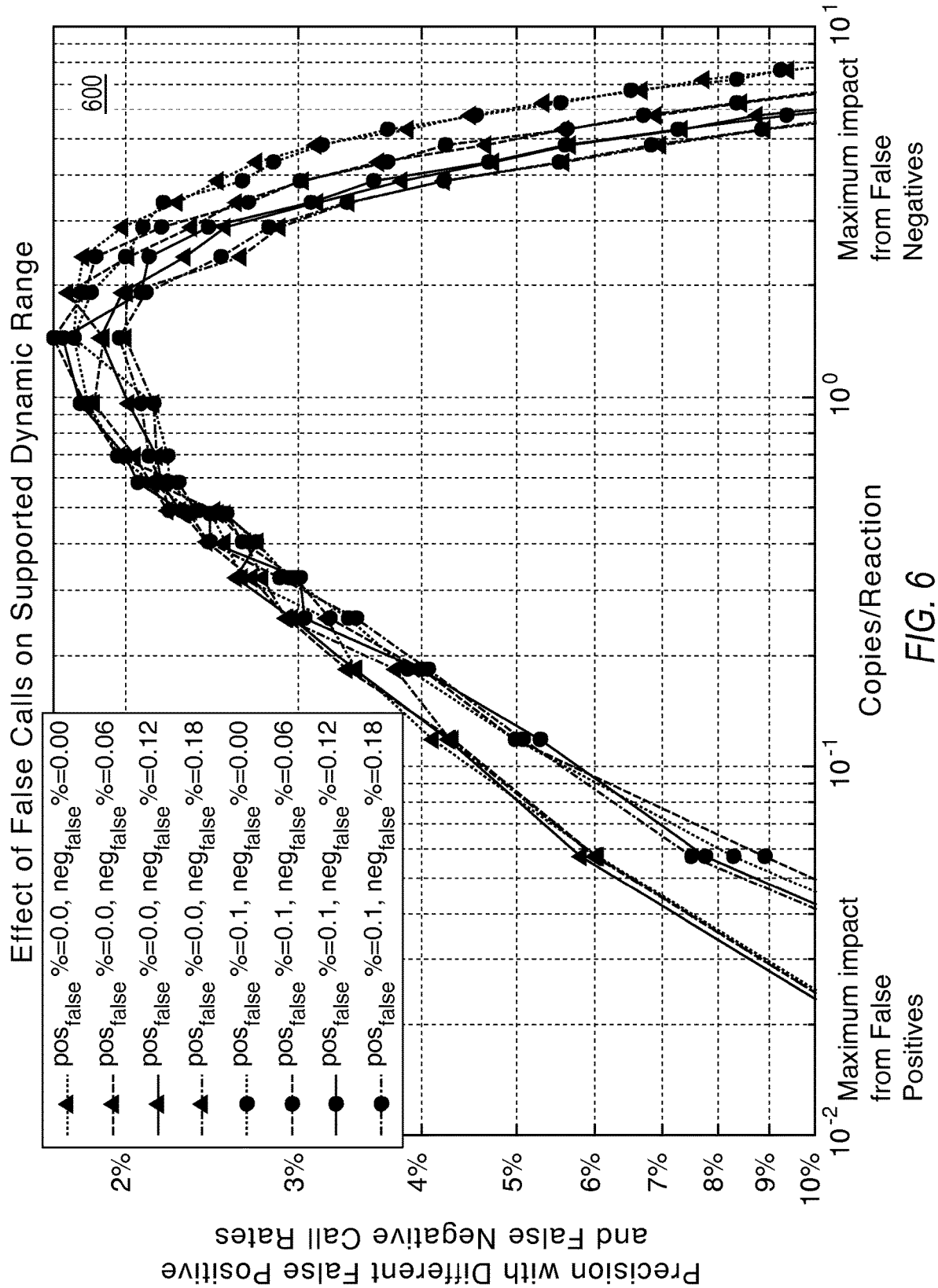
FIG. 6 illustrates the relationship of precision with false calls according to various embodiments described herein.

FIG. 6 illustrates a graph 600 showing that precision degrades with false calls (false positives impact the lower end while false negatives impact the higher end of detectable concentrations.

Figure 7:
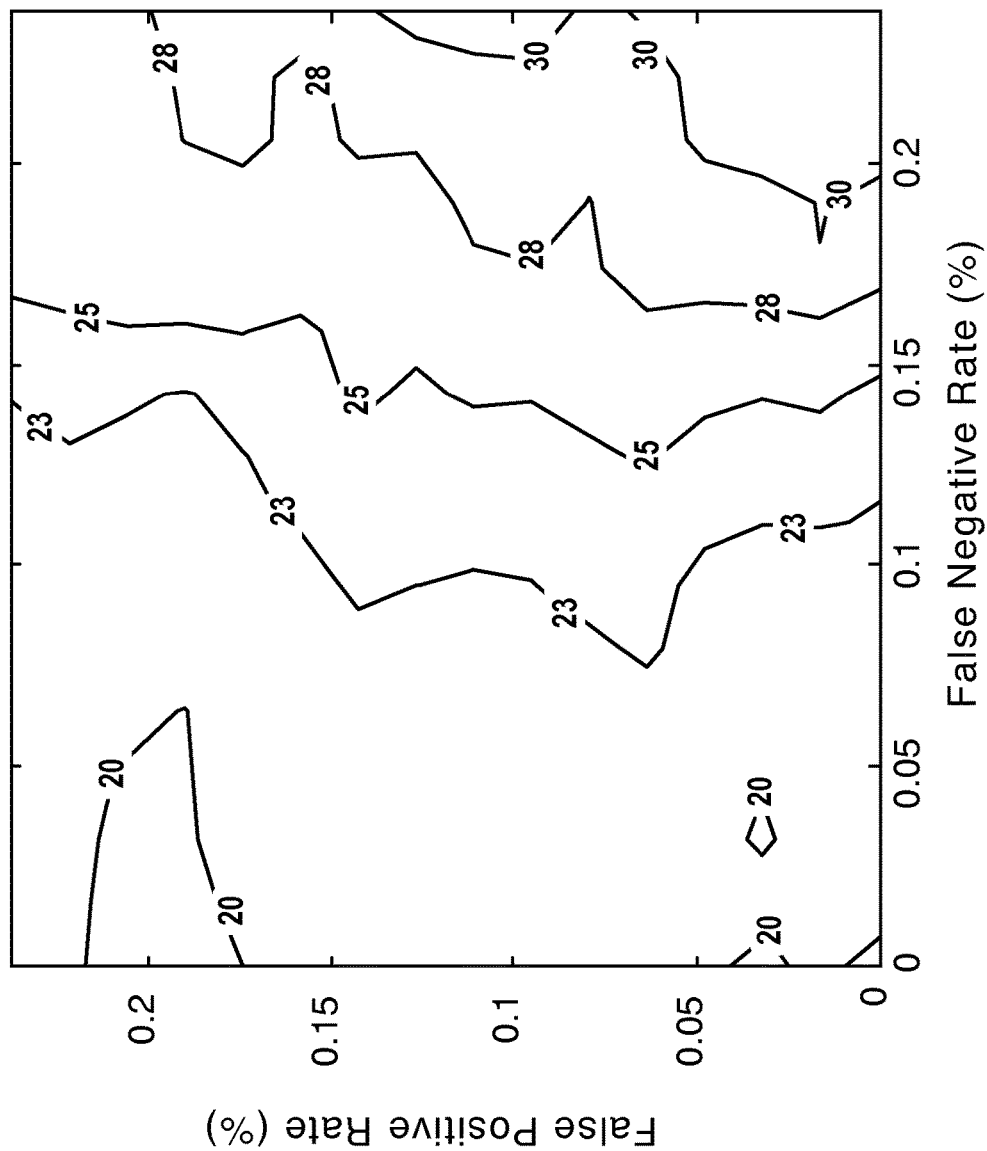
FIG. 7 illustrates contours showing the desired load for optimal precision under the influence of nonzero false positives and false negatives according to various embodiments described herein.

FIG. 7 illustrates example contours useful for determining how to recover from noise factors by targeting different percent negatives for best measurement precision. As mentioned above, under the influence of zero false call rates, the percent negatives affording best precision is at 20% negatives. However, as the false negative rate increases, it is desirable to target a higher percent negatives for optimal measurement precision. The labels of the contours present load concentration values for best precision in percent negatives.

Figure 8:
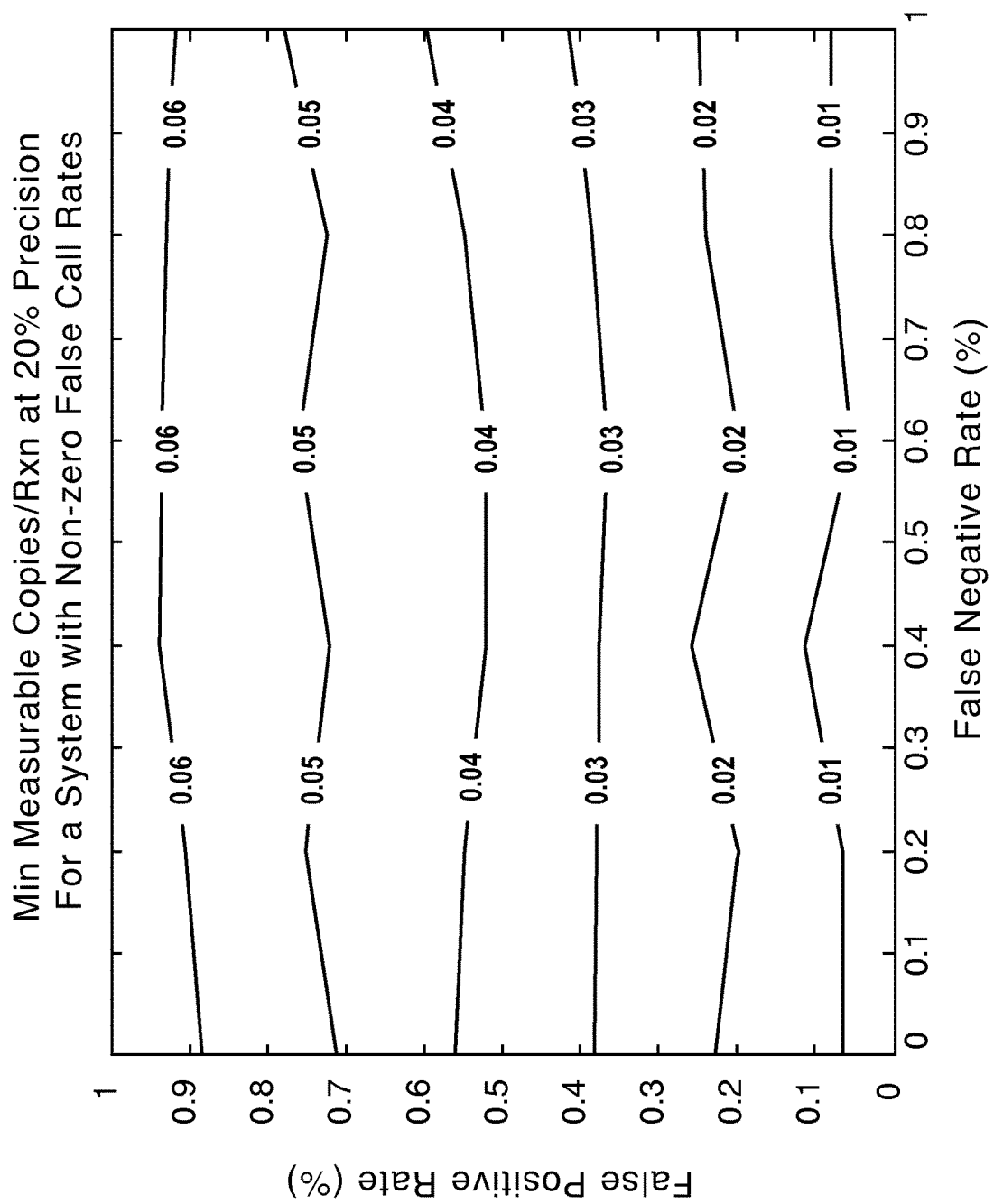
FIG. 8 illustrates contours showing the lower limit of detection under the influence of false positive and false negative calls according to various embodiments described herein.

FIG. 8 illustrates a graph showing that lowering the false positive calls improves the lower limit of detection. The labels of the contours present the minimum detectable copies/reaction values at 20% detection precision.

The impact from reaction dropouts due to a variety of causes including, but not limited to, quality considerations such as presence of dust or debris are also investigated using Monte Carlo simulations.

Figure 9:
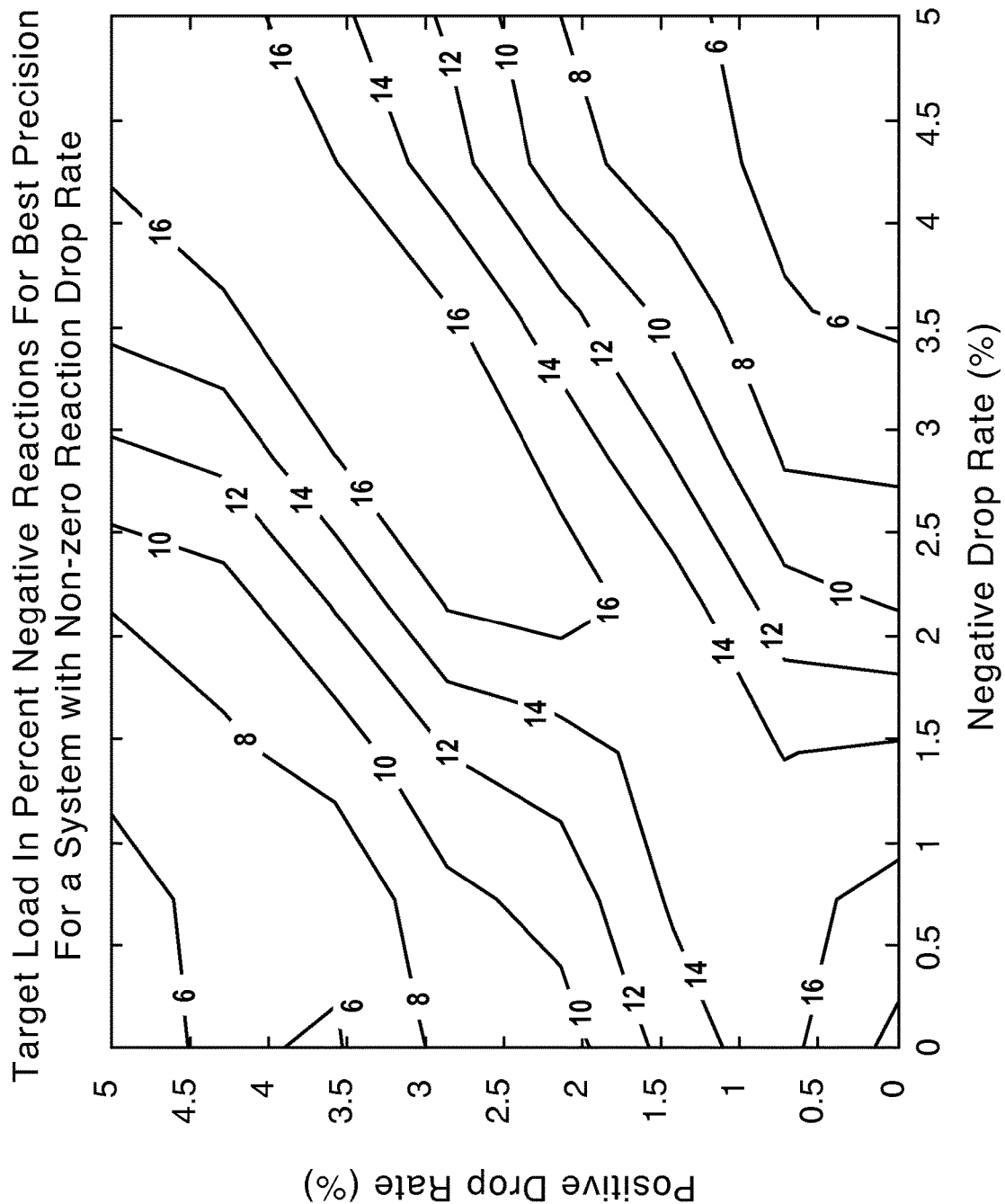
FIG. 9 illustrates contours showing the desired load concentrations to compensate for positive/negative reaction loss according to various embodiments described herein.

FIG. 9 illustrates contours with desired load concentrations for measurement with best precision when compensating for positive/negative reaction loss. For an ideal system, the peak measurement precision was derived to be at 20% negatives. Thus, the same positive drop rate impacts a larger number of actual reaction sites for dropped positive reaction sites versus dropped negative reaction sites around the best measurement precision point. This is evidenced from the fact that rate of change is faster with increase in the positive drop rate versus increase in the negative drop rates. To recover from this effect, simulations suggest moving to higher loading sample concentrations for both positive and negative reaction drops. The labels of the contours present load concentration values for best precision in percent negatives.

Figure 10:
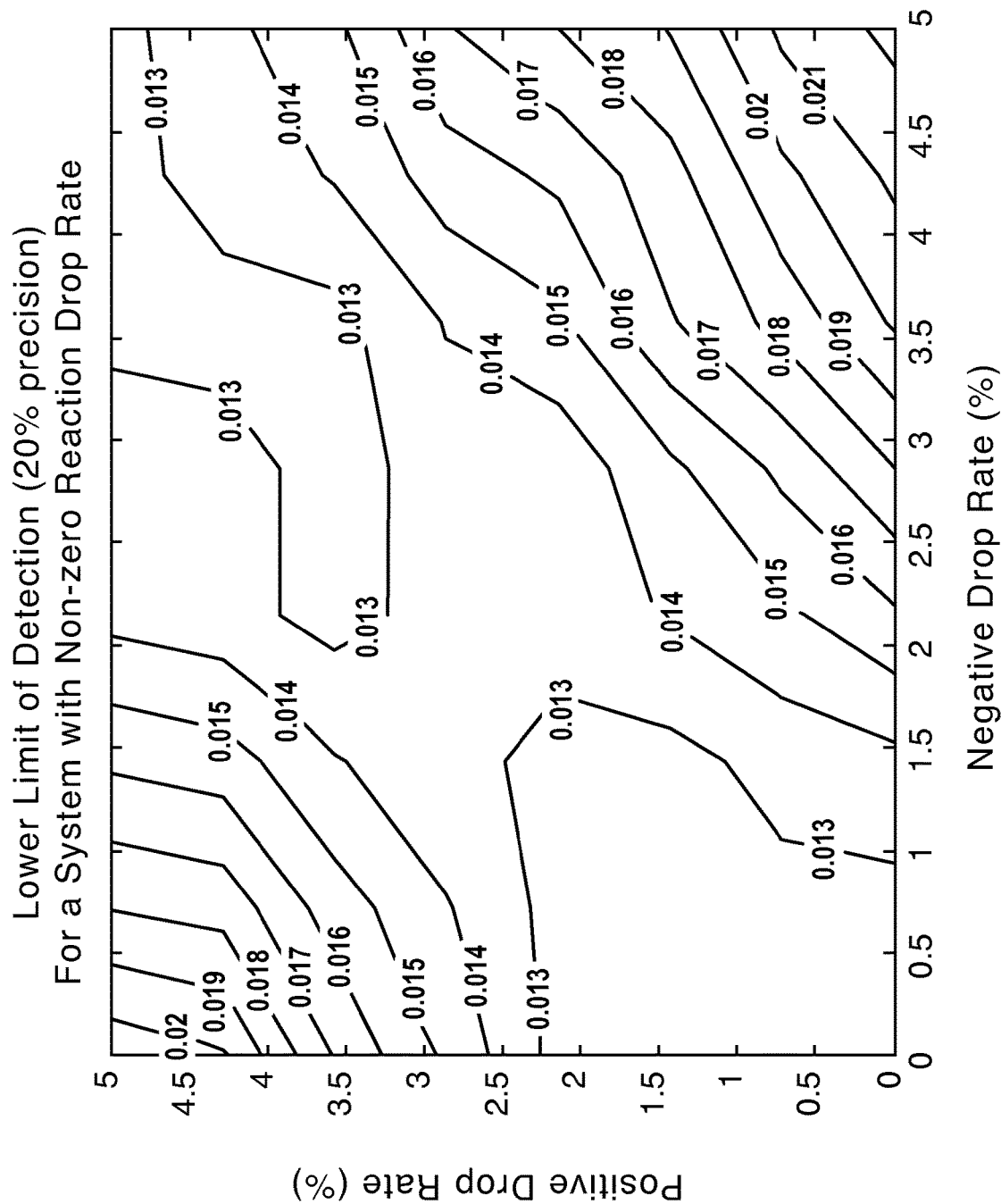
FIG. 10 illustrates contours showing the lower limit of detection under the effect of reaction dropouts according to various embodiments described herein.

FIG. 10 illustrates a lower bias toward rejection of negative reactions to reduce impact to the lower limit of detection. The labels of the contours present the minimum detectable copies/reaction values at 20% precision.

The effect of volumetric variation among reaction sites on estimating the concentration was investigated with Monte Carlo simulations. More volume is represented by increased probability of a reaction site containing a molecule. Normal distribution of volume variation is assumed with the standard deviation taken as a percentage of the mean volume.

Figure 11:
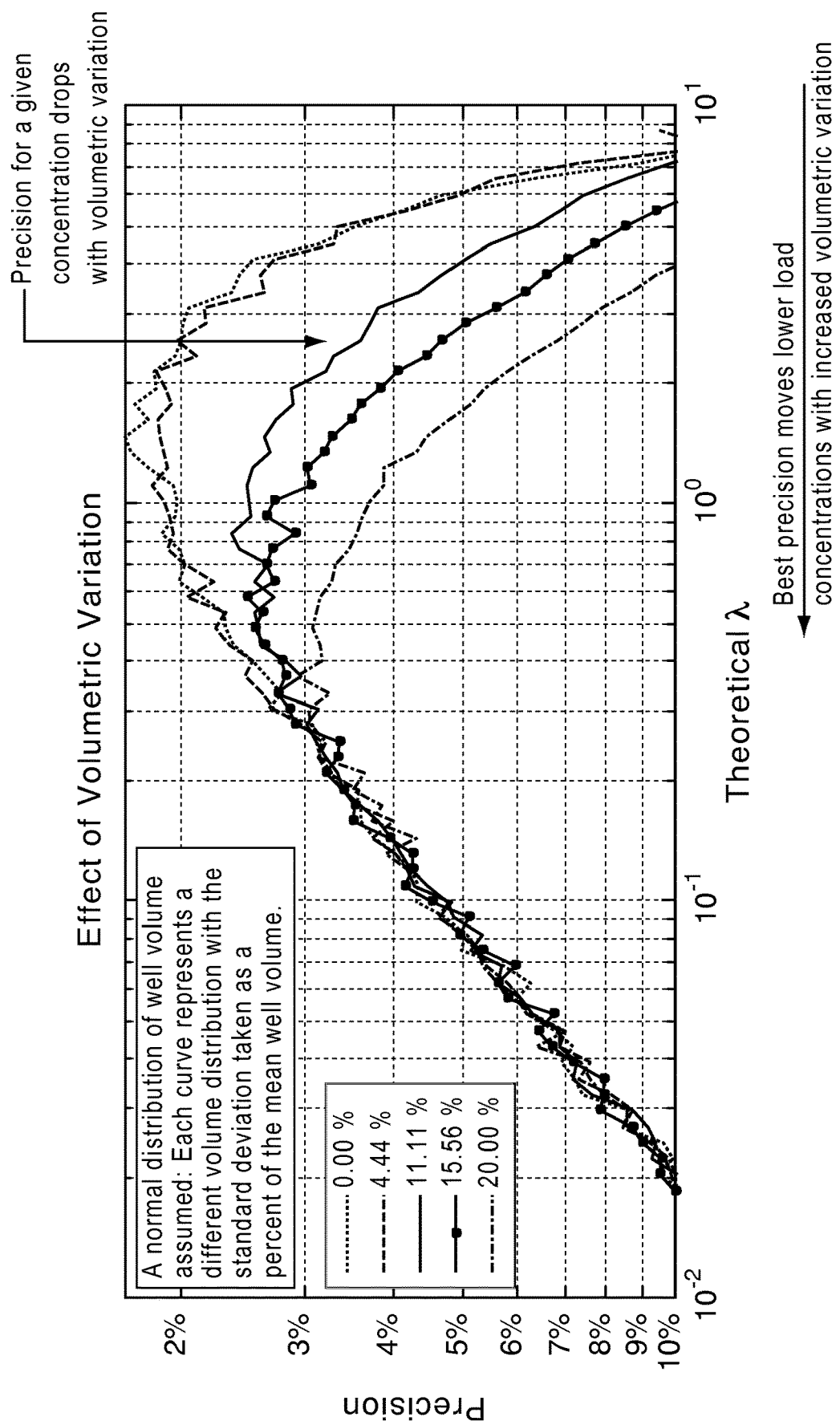
FIG. 11 illustrates a graph showing how volumetric variations in partition sizes deteriorate measurement capability at the higher concentration according to various embodiments described herein.

FIG. 11 illustrates the volumetric variations in reaction volumes deteriorate measurement capability at higher concentrations of the target.

Figure 12:
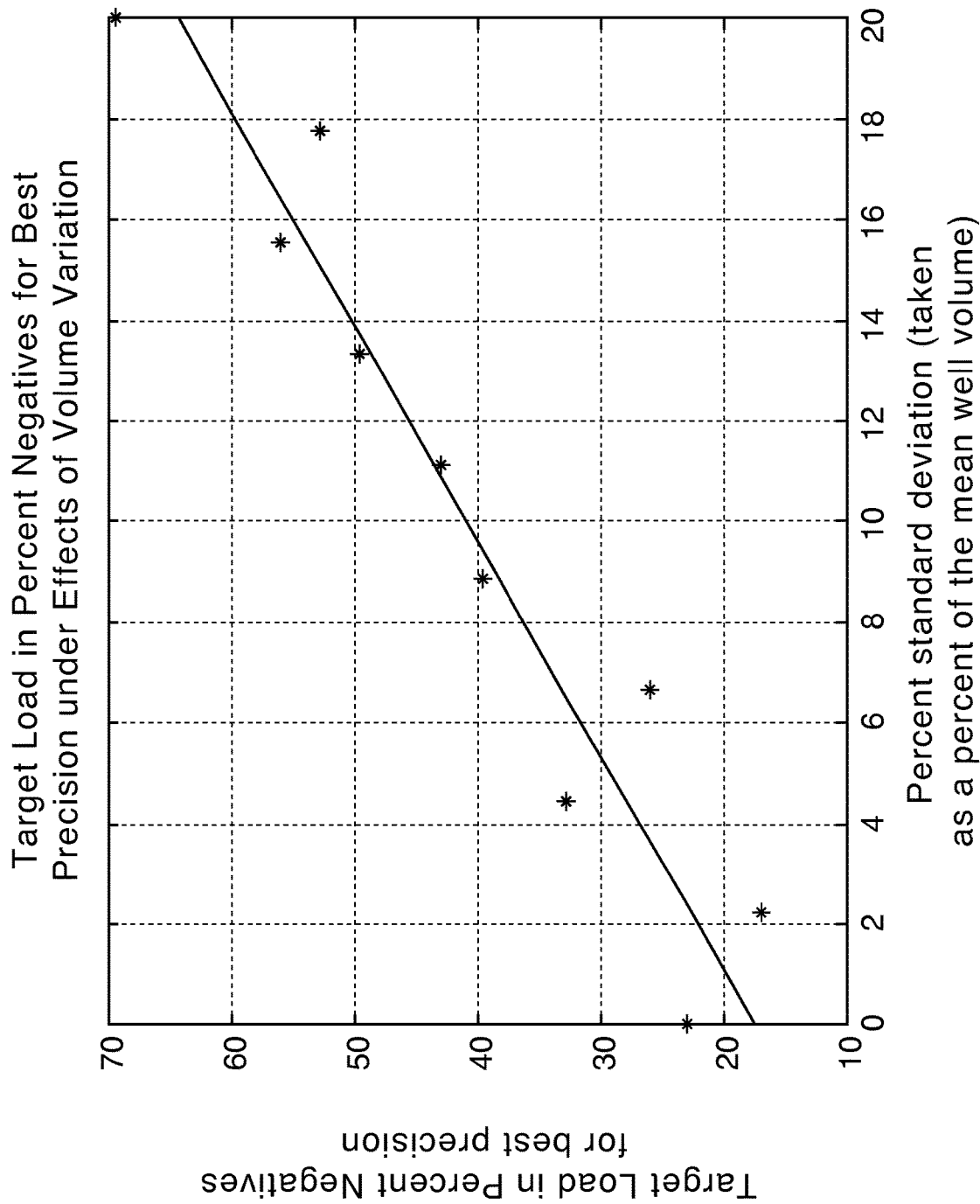
FIG. 12 illustrates a graph showing the target load in percent negatives for best precision to compensate for partition size variation according to various embodiments described herein.

FIG. 12 illustrates the target load in percent negatives for best precision to compensate for partition size variation.

Extending the Dynamic Range Using Dilutions

Figure 13:
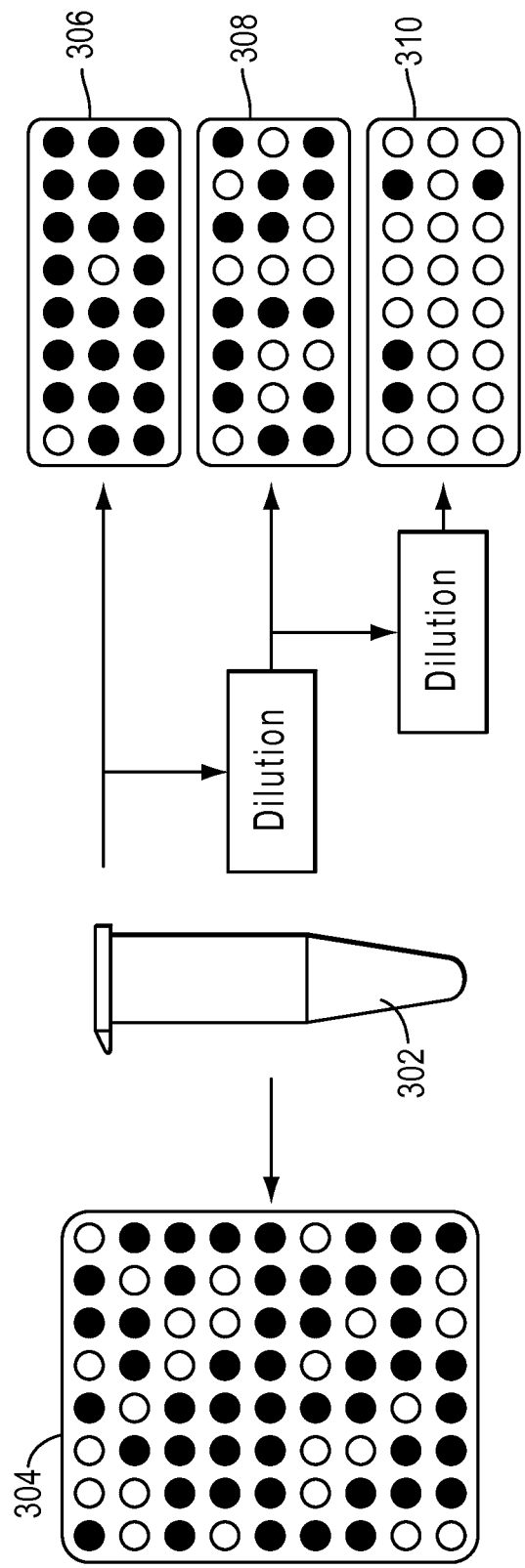
FIG. 13 illustrates an example of multiple dilutions with partitioning according to embodiments described herein.

The error modeling in the previous section showed how the theoretical dynamic range is depressed by noise factors. One way to mitigate this problem and enhance the dynamic range from digital PCR experiments is by running one or more dilution points. FIG. 13 illustrates an exemplary dPCR workflows. Sample 302 may be partitioned into a plurality of reaction sites as shown in substrate 304. Sample 302 may be diluted at least once and partitioned into reaction sites. In FIG. 13, sample 302 is diluted once and loaded into a set of reaction sites in substrate 306. Further, the sample may be diluted a second time and loaded into a second set of reaction sites in substrate 308. Sample 302 may be diluted a third time and loaded into a third set of reaction sites in substrate 310. In examples, at least one dilution is performed on a sample to increase dynamic range and precision, according to various embodiments of the present teachings.

Figure 14:
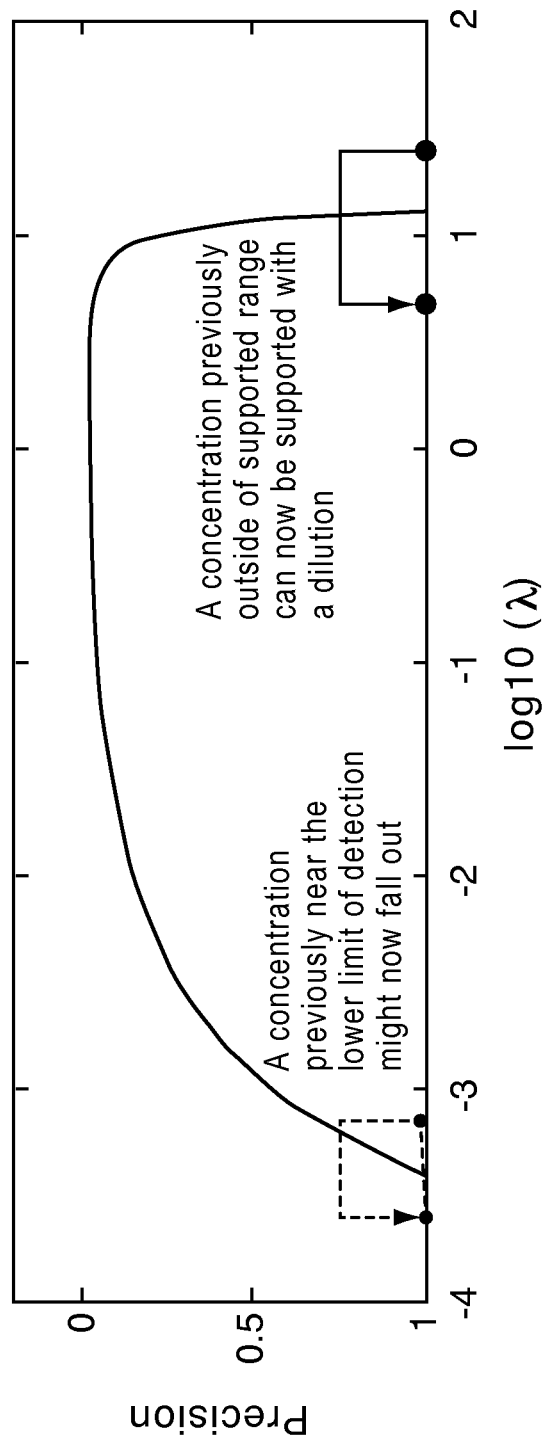
FIG. 14 illustrates the effect of dilutions on detection of a target in a dPCR system according to various embodiments described herein.
Figure 15:
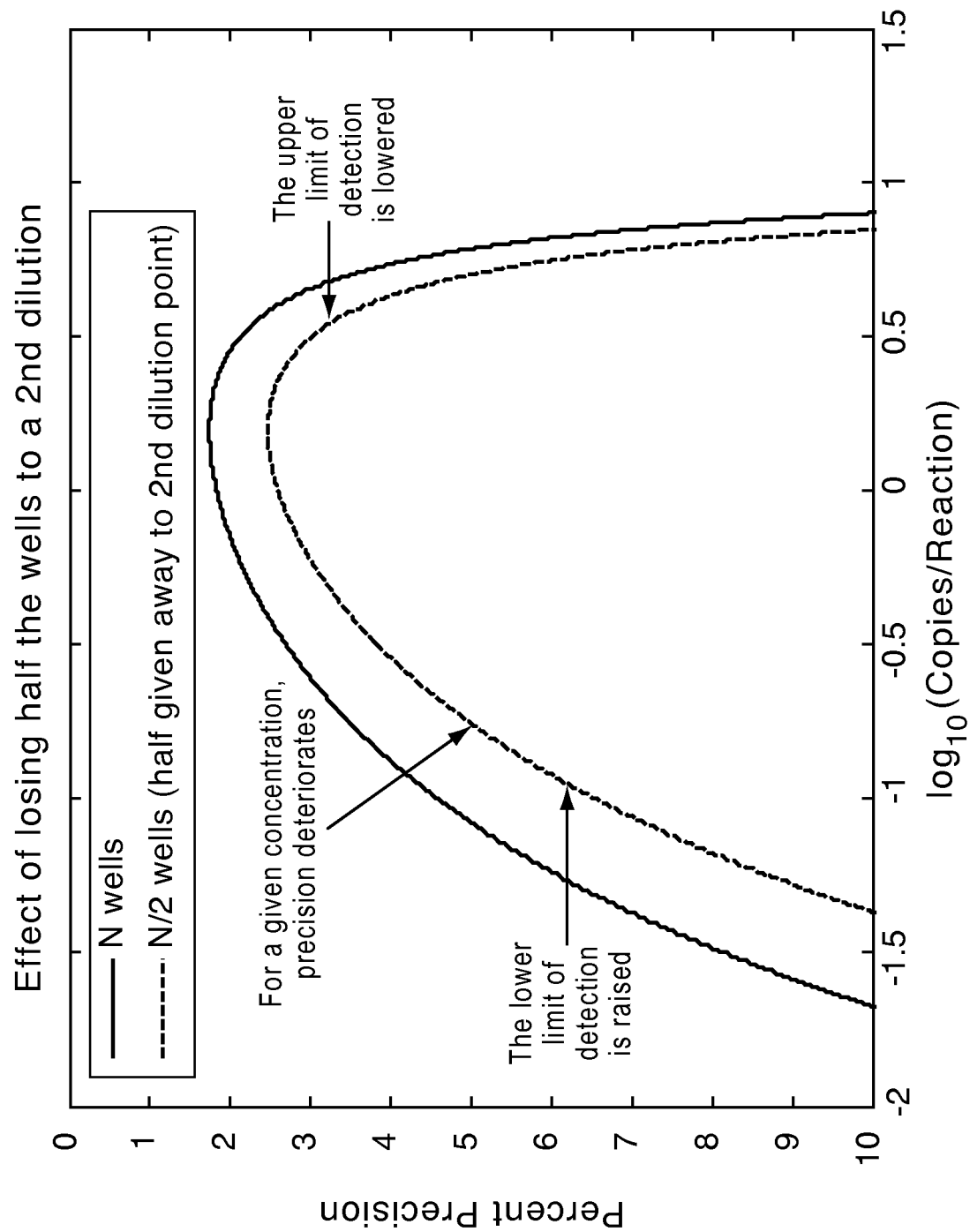
FIG. 15 illustrates a plot showing the effect of dilution on the lower limit of detection and the dynamic range from a single substrate according to various embodiments described herein.

FIG. 14 illustrates the effect of dilutions on precision. Dilutions help detect samples of concentrations higher than a supported range, but may put samples near the lower limit of detection outside of supported range. Further, dilutions used in various combination of dilutions extend the dynamic range with the original concentration of a sample preserving the detection of the rare target and the dilution point enabling the detection the abundant targets. FIG. 15 illustrates a plot showing the effect of dilution on the lower limit of detection and the dynamic range for a single substrate when half the reaction sites are donated to a second dilution point.

The impact on the lower limit of detection due to splitting of available reactions between two dilutions is illustrated as follows:

$$\lambda_{LLOD\_Diluted} = -\ln((1-C)^{2/n}) = -2*\ln((1-C)^{1/n}) = 2*\lambda_{LLOD} > \lambda_{LLOD} \quad (16)$$

The impact on the upper limit of detection due to splitting of available reactions between two dilutions is illustrated as follows:

$$\lambda_{ULOD\_Diluted} = -\ln(1-(1-C)^{2/n}) < -\ln(1-(1-C)^{1/n}) = \lambda_{ULOD} \quad (17)$$

Figure 17:
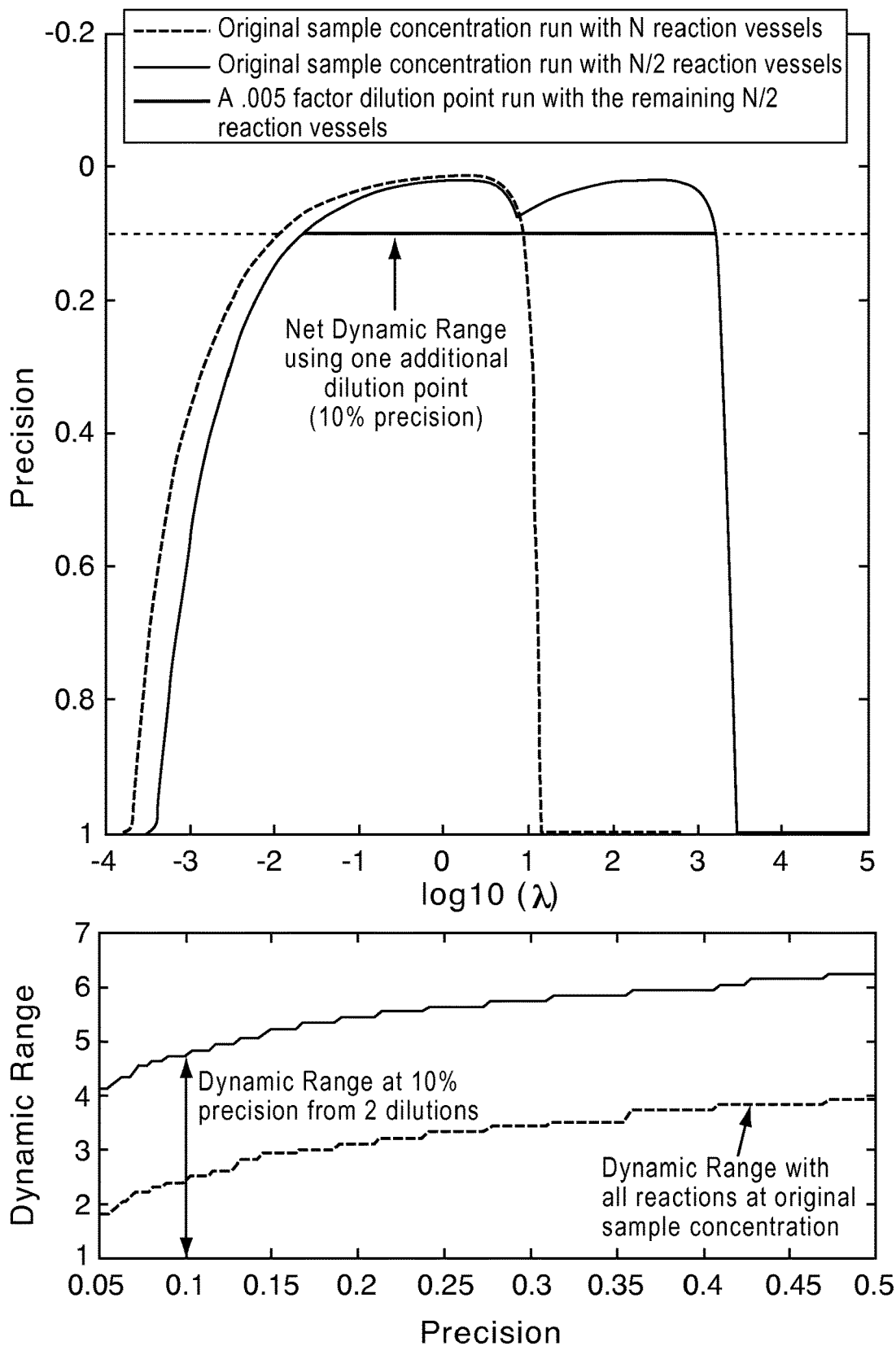
FIG. 17 illustrates an increase in dynamic range with dilutions according to various embodiments described herein.

FIG. 17 illustrates an example where the greater dynamic range afforded with one additional dilution using 20K reaction sites. In this example, the original sample was run with an additional dilution point, to take advantage of detection range from the original concentration point and the detection range from the dilution point. However, as shown in equation 16 and 17, if splitting available reactions between dilutions, there will be slight rise in lower limit of detection due to fewer available reaction sites dedicated to sample volumes at the original concentration. However, higher concentrations are now detectable from the set of reactions with the diluted sample. To try to achieve meeting the precision requirement from the system for any answer, the upper x % of the dynamic range from the original concentration point is overlapped with the lower y % of the dynamic range from the dilution point, ensuring continuous detection at required precision.

Figure 16A:
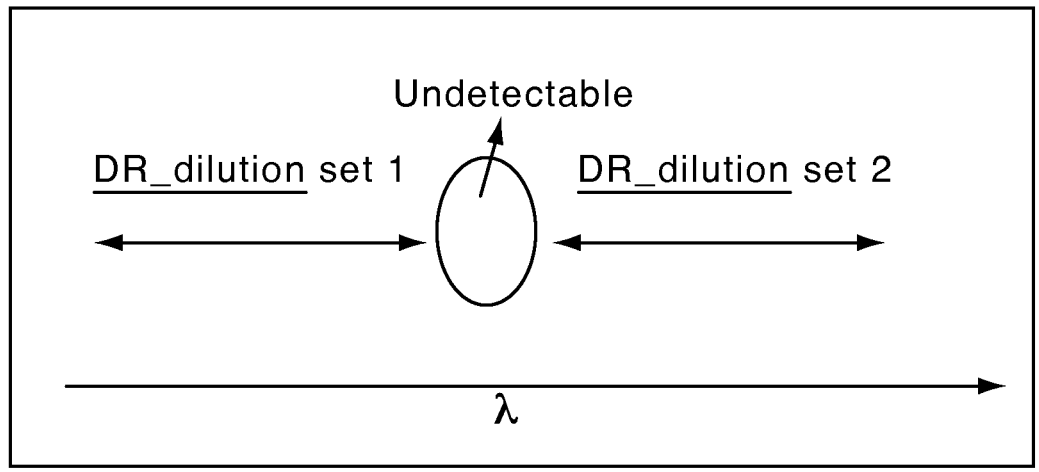
FIGS. 16A and 16B illustrate the constraints on dilution factors for continuous detection when using a combination of multiple dilutions according to various embodiments described herein.
Figure 16B:
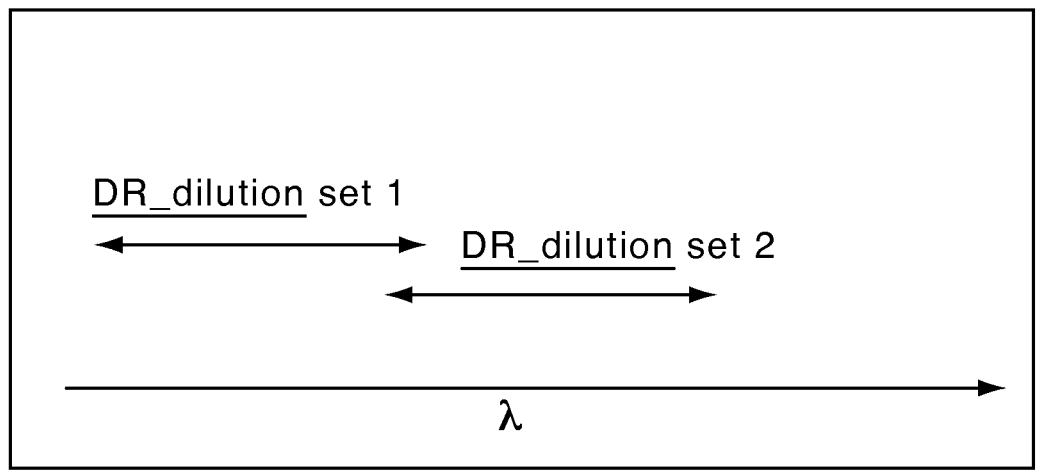

FIGS. 16A and 16B illustrates the limit on dilution factors described above. Let the two dilution points be named dilution points 1 and 2, where dilution point 1 is more concentrated than dilution point 2. For a continuous detection ability between the two dilution points, the second dilution point can have its lower limit of detection less than or equal to the upper limit of detection from the first dilution point. Otherwise, there may be a discontinuous gap as indicated in FIGS. 16A and 16B. This indicates there is a limit on the lowest concentration one may dilute to if one needs to be able to continuously detect between the LLOD of the first dilution point and the ULOD of the second dilution point.

Figure 18A:
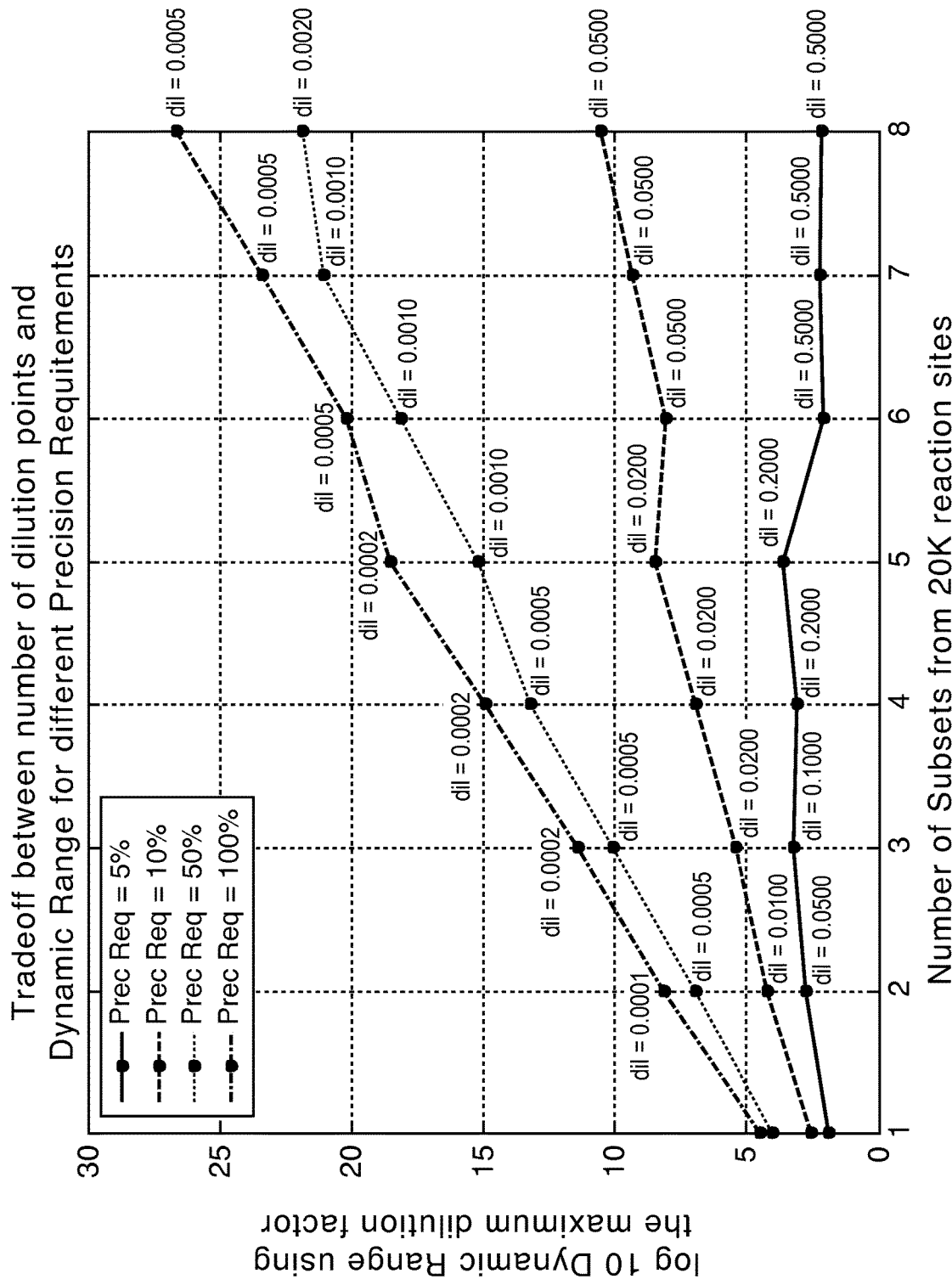
FIGS. 18A, 18B, and 18C illustrate the tradeoff between the number of dilution points and the increase in the dynamic range according to various embodiments described herein.
Figure 18B:
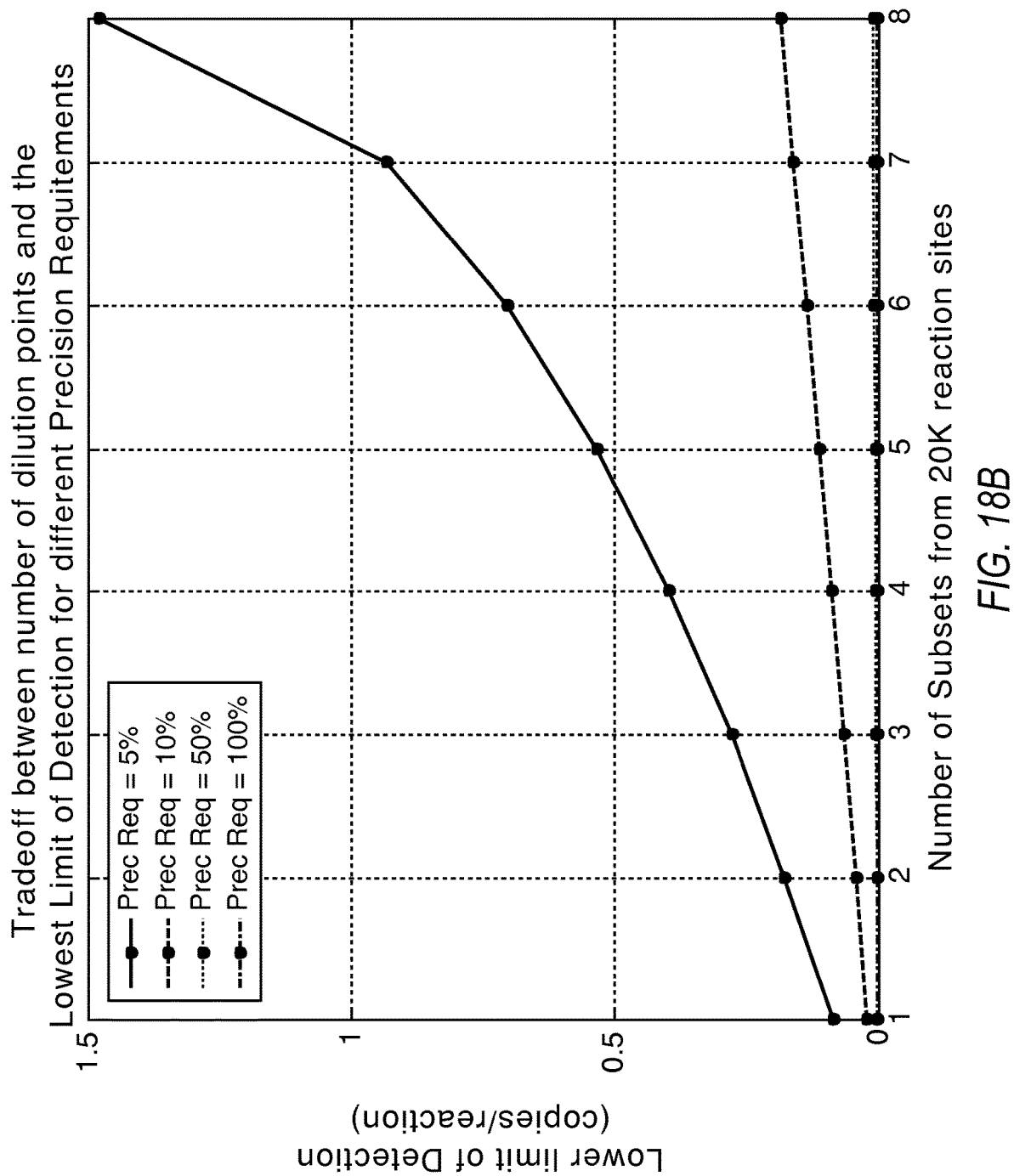
Figure 18C:
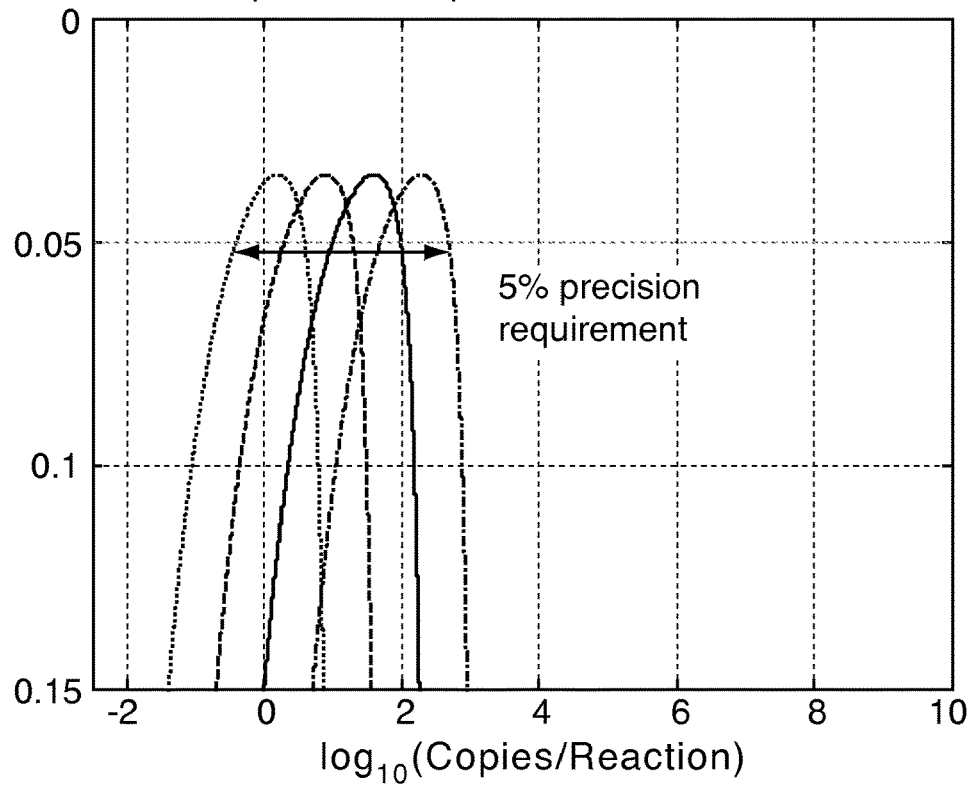
Figure 18C:
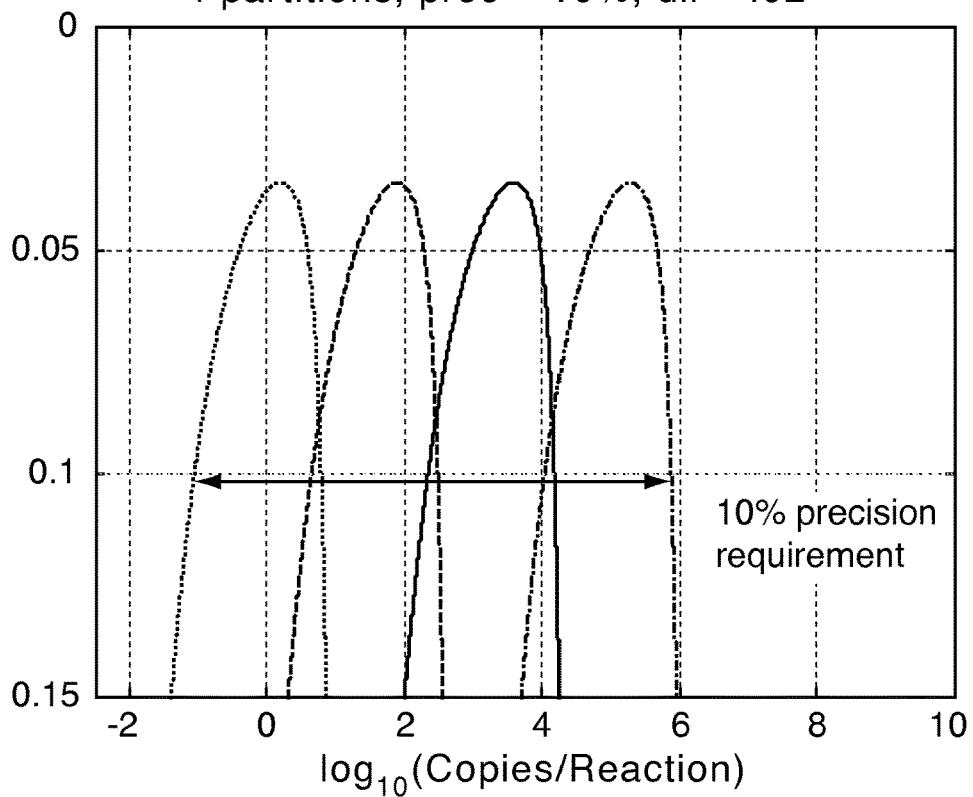

There exists a tradeoff between the required precision, the lower limit of detection, and the use of additional dilutions to extend the dynamic range. FIG. 18A illustrates how additional dilutions can extend the dynamic range from the system beyond using just two dilutions. 20K reaction sites were split in equal partitions in this simulation. FIG. 18B shows the impact to the lower limit of detection as wells from the initial dilution get distributed to additional dilution points. It can be seen that more than two dilution points at 5% precision produces limited additional dynamic range. However, as the precision requirement is dropped, substantial gains in dynamic range are possible with more dilution points. These gains in dynamic range are conditional upon a willingness to accept a deterioration to the lower limit of detection. Also, performing the dilutions may introduce additional source of variation, which could in turn limit the effective precision of the system. FIG. 18C shows the effect of introducing four dilution points with 5% and 10% precision requirements as examples.

Using the foregoing teachings, methods may be implemented by a computing system to provide a dPCR experiment designer tool to a user according to various embodiments of the present teachings. A user may be able to more easily plan a desired experiment based on the outputs provided by the dPCR experiment designer. Further, after both the Dynamic Range Expansion related dilution factors or the Target Digital PCR related dilution factors are estimated, a further set of calculations are employed to suggest stock-to-reaction mix dilution factors to convert from stock concentration to targeted dPCR reaction mix dilution. These calculations are described in the following section.

Stock-to-Reaction Mix Dilution Factor—Stock Concentration to Targeted Dper Dilution Factor According to various embodiments, a dPCR experiment designer may further be used to calculate stock-to-reaction mix dilution factors for diluting a stock sample to a targeted dPCR dilution factor, also calculated by the dPCR experiment designer. In other words, a dPCR experiment designer may further assist a user in performing a desired experiment by providing additional dilution factors for a user to dilute a stock solution of a known concentration to the desired concentration based upon dynamic range and/or precision requirements, for example.

Calculation of the stock-to-reaction mix dilution factors are based on parameters such as the desired volume of the dPCR reaction, the concentrations of reaction reagents, and minimum pipette volumes for both sample and reaction reagents. Furthermore, the stock-to-dilution dilution factors may be further based on the appropriate volumes of each of the reaction components to add to the reaction mix in order to get the stock sample to the targeted dPCR reaction mix dilution. The stock-to-reaction mix dilution factors may also be based on the minimum pipette volumes in order to determine any initial dilutions of the sample or assays (prior to their addition to the reaction mix) necessary to achieve the target dPCR reaction mix dilution of the sample. A minimum pipette volume may be needed to consider because the capability of a pipette, such as the limitations of volume to be dispensed accurately from a pipette, may affect the user's ability to prepare a sample. Taking into account these factors, the user may need to input the following parameters, for example, into the dPCR experiment designer to calculate the stock-to-reaction mix dilution factors according to various embodiments.

Input Parameters
Targeted dPCR Dilution Factor in dPCR Reaction Mix for the Sample
Minimum Sample Pipet volume
Minimum Reagent Pipet volume
Desired Total Reaction volume
Non-diluted Master Mix concentration
Assay List
Non-diluted Assay concentrations The results of the stock-to-reaction mix dilution portion of the dPCR experiment designer may be a list of reaction component volumes (and any necessary pre-dilution factors) to be added to the reaction mix which produces the targeted dPCR reaction mix dilution of the sample according to various embodiments. The provided component volumes by the dPCR experiment designer may satisfy the minimum pipette volume constraints. For example, the output of the dPCR experiment designer may include, but is not limited, to the following:

Output
Initial Sample Dilution Factor (outside of dPCR Reaction Mix)
Initial Assay Dilution Factor (outside of dPCR Reaction Mix)
Volume and final concentration in mix for
   Master Mix
   Initially Diluted Assays
   Initially Diluted Sample
   Water
Total Volume According to various embodiments, method to determine the stock-to-reaction mix dilution factors includes a first step of checking if the final sample dilution factor is possible. The second step may include calculating the initial dilution factor of the sample and assays. The third step may include setting the test volume as the desired volume for the experiment. The fourth step may determine various parameters until the assay concentrations are equal to 1×. The fifth step may include providing the results to the user, including: initial dilution factor of sample, initial dilution factor of assay(s), final master mix volume, final assay volume(s), final sample volume, and final water volume. An example of the method determining the stock-to-reaction mix dilution factors is as follows:

Step 1: Check if Final Sample Dilution Factor possible.
  a. Compute volume left over after reaction reagents have been accounted for.
  b. If Final Sample Dilution Factor greater than percentage of remaining volume, return Step 2: Calculate Initial Dilution Factor of Sample and Assays
  a. Calculate Minimum Reaction Volume needed based on Reagent Concentrations and minimum pipette volume for reagents
  b. Calculate initial Master Mix volume
  c. Calculate initial Assay volumes
  d. Determine if Sample volume at desired dilution fits in remaining volume
    i. If so, conduct simple Sample volume computation fitting Sample into remaining volume
    ii. If not, compute surplus Sample volume needed to achieve Final Sample Dilution Factor
  e. Calculate initial Dilution Factor of Sample based on computed Sample volume in 2d f. Calculate initial Dilution Factor of Assay(s) based on Desired Total Reaction Volume, Minimum Reaction Volume, and Final Sample Dilution Factor Step 3: Set Test Volume=Desired Volume Step 4: Cycle until Reagent Concentrations equal 1×
   a. Calculate Final Master Mix volume
   b. Calculate test Assay volume(s)
   c. Calculate test Sample volume
   d. Calculate test Water volume
   e. Recalculate Initial Dilution Factor of Sample
   f. Recalculate Initial Dilution Factor of Assay(s)
   g. Recalculate Final Assay volume(s) based on recomputed Initial Dilution Factor of Assay(s)
   h. Recalculate Final Sample volume based on recomputed Initial Dilution Factor of Sample and Minimum Sample Pipette volume.
   i. Compute Final Water volume
   j. Compute test Final Volume (max of Test Volume and sum of Master Mix, Assay, Sample, and Water volumes)
   k. If any Assay concentration not equal to 1, increment the Test Volume Step 5: Return Initial Dilution Factor of Sample, Initial Dilution Factor of Assay(s), Final Master Mix volume, Final Assay volume(s), Final Sample volume, and Final Water volume.

dPCR Experiment Designer Uses

The dPCR experiment designer is a tool buit based on the above digital PCR model has three typical workflows for digital PCR experiments. If a user has alternate information in terms of a nanodrop readings or a Ct value from a previous qPCR experiment, the dPCR experiment designer can be used to calculate the target digital PCR dilution factor by inputting that information. Further, the dPCR experiment designer may generate a recommendation for the user for the reaction mix for the digital PCR experiment.

Alternately, the dPCR experiment designer can be used to generate recommendations for the PCR mix for a digital PCR experiment performed across two substrates at two different concentrations. This would support a gene expression quantification workflow across a desired dynamic range, for example.

For rare target detection, the dPCR experiment designer can provide recommendations for the number of substrates, each including a predetermined number of reaction sites, needed to detect a desired fold change at a certain confidence level. This would support, as an example, a rare mutation detection workflow using a dual reporter SNP assay.

Figures 1, 20A:
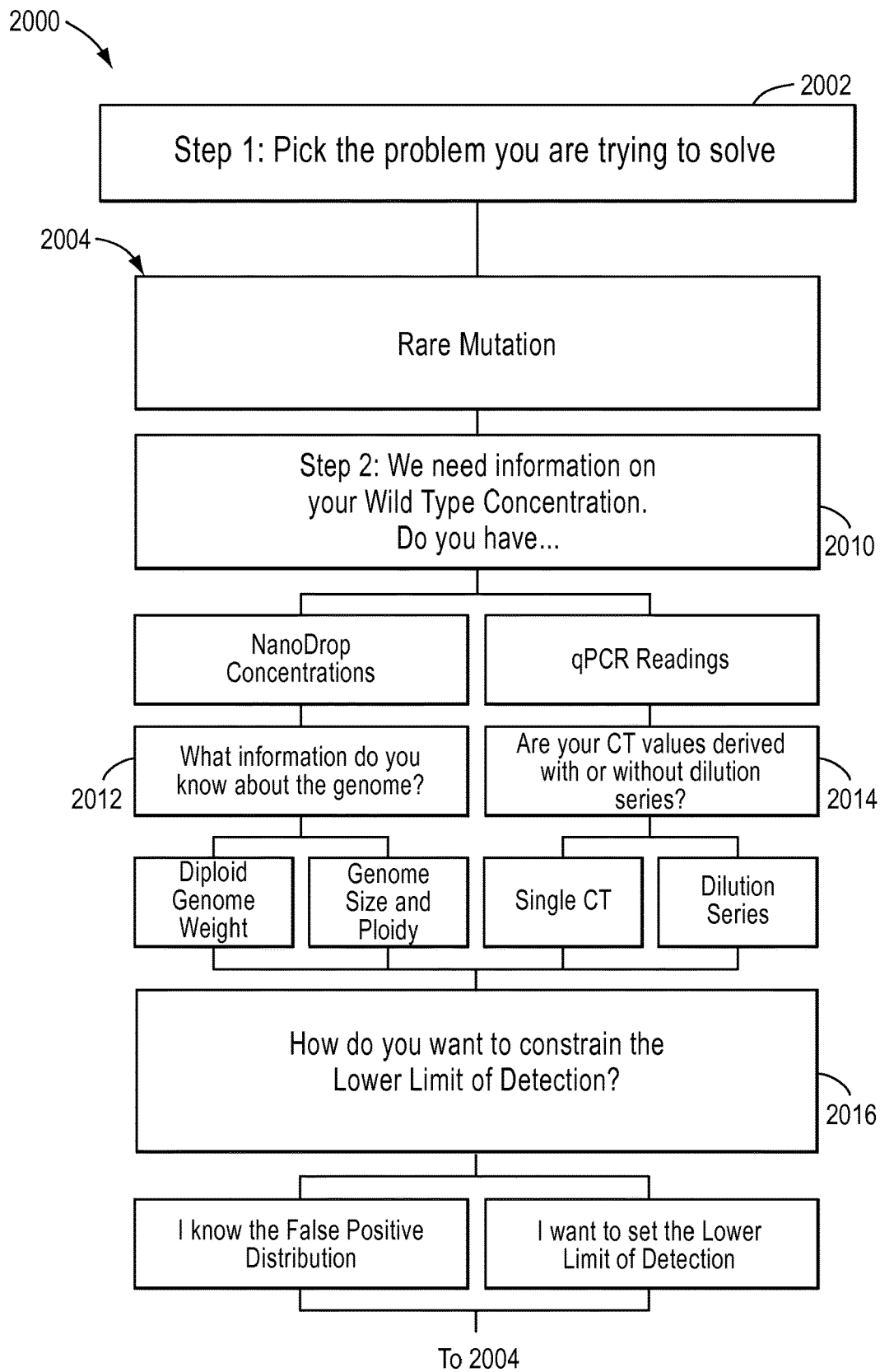
FIG. 20A and FIG. 20B illustrate a flow chart with the various digital PCR methods implemented by a dPCR experiment designer according to various embodiments described herein.
Figures 2, 20A:
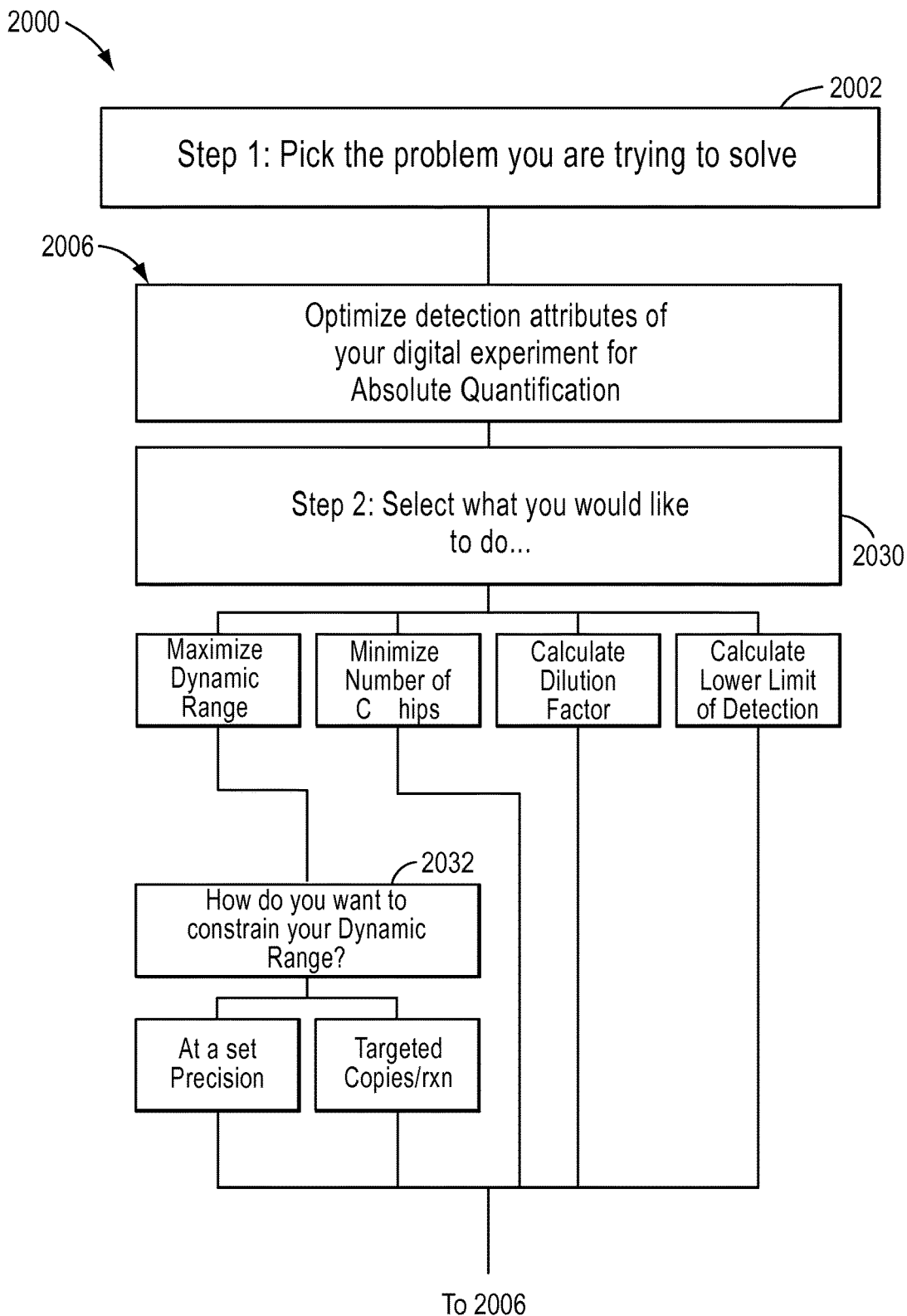
Figures 3, 20A:
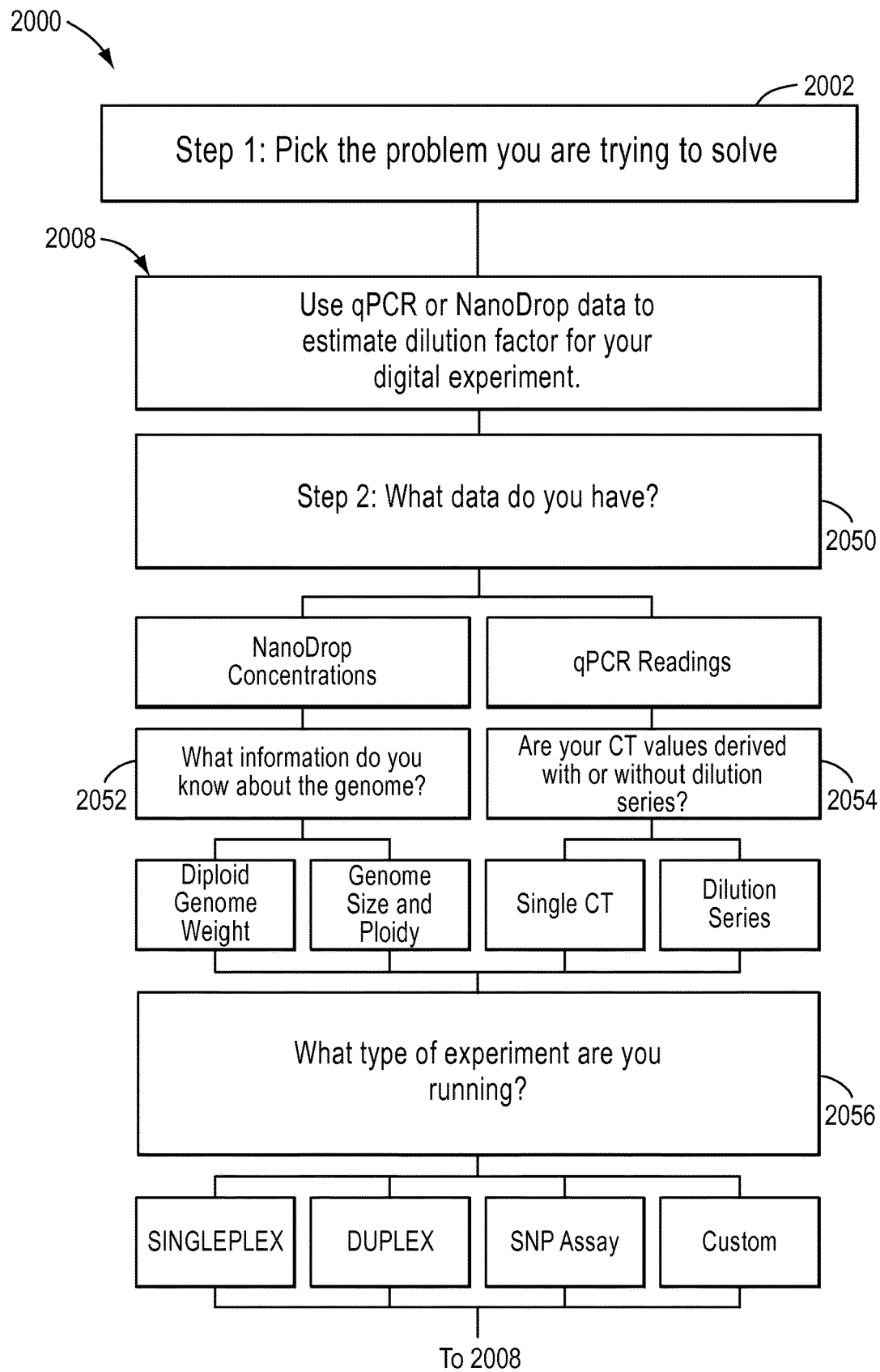
Figures 1A, 20B:
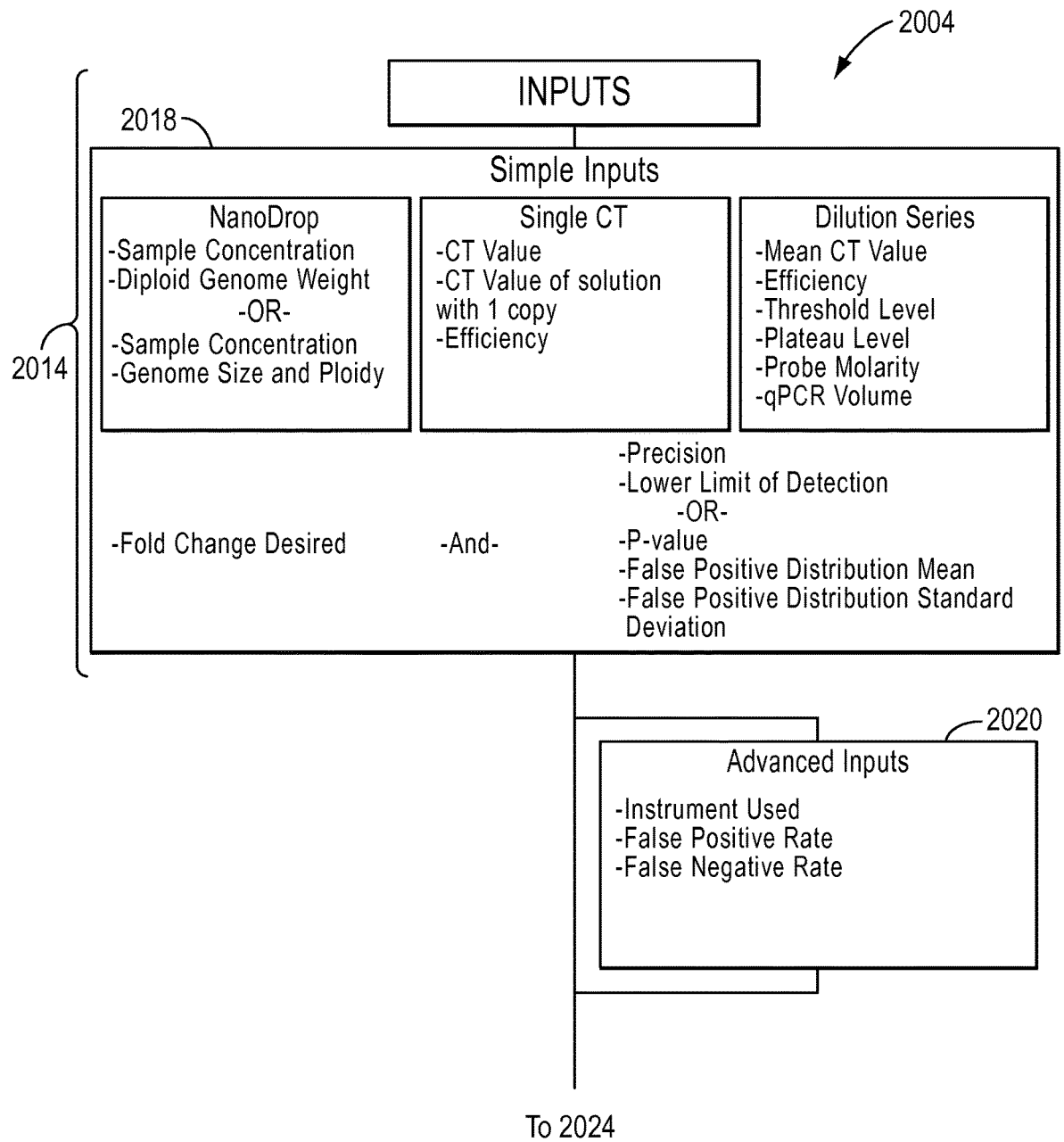
Figures 1B, 20B:
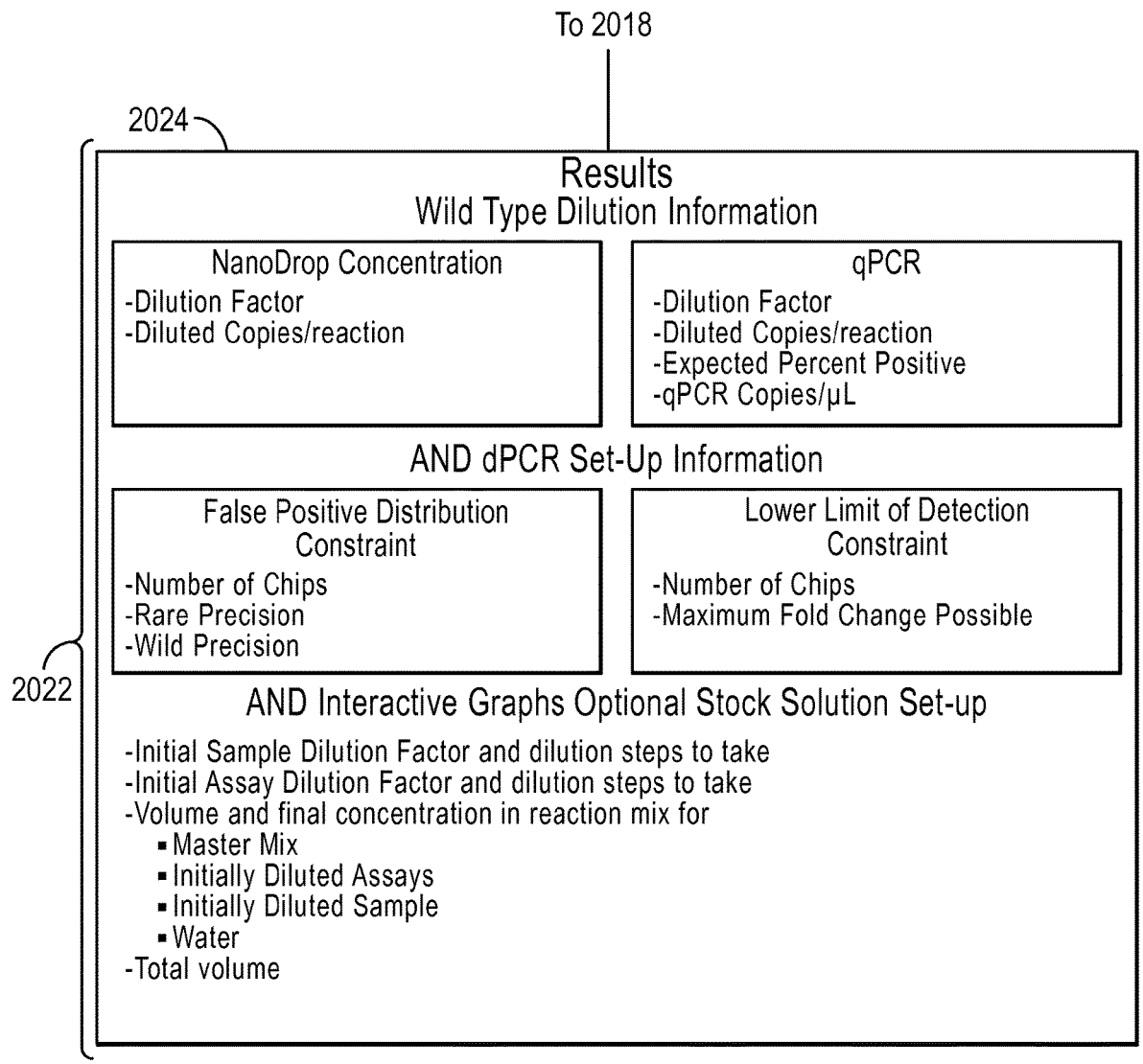
Figures 2A, 20B:
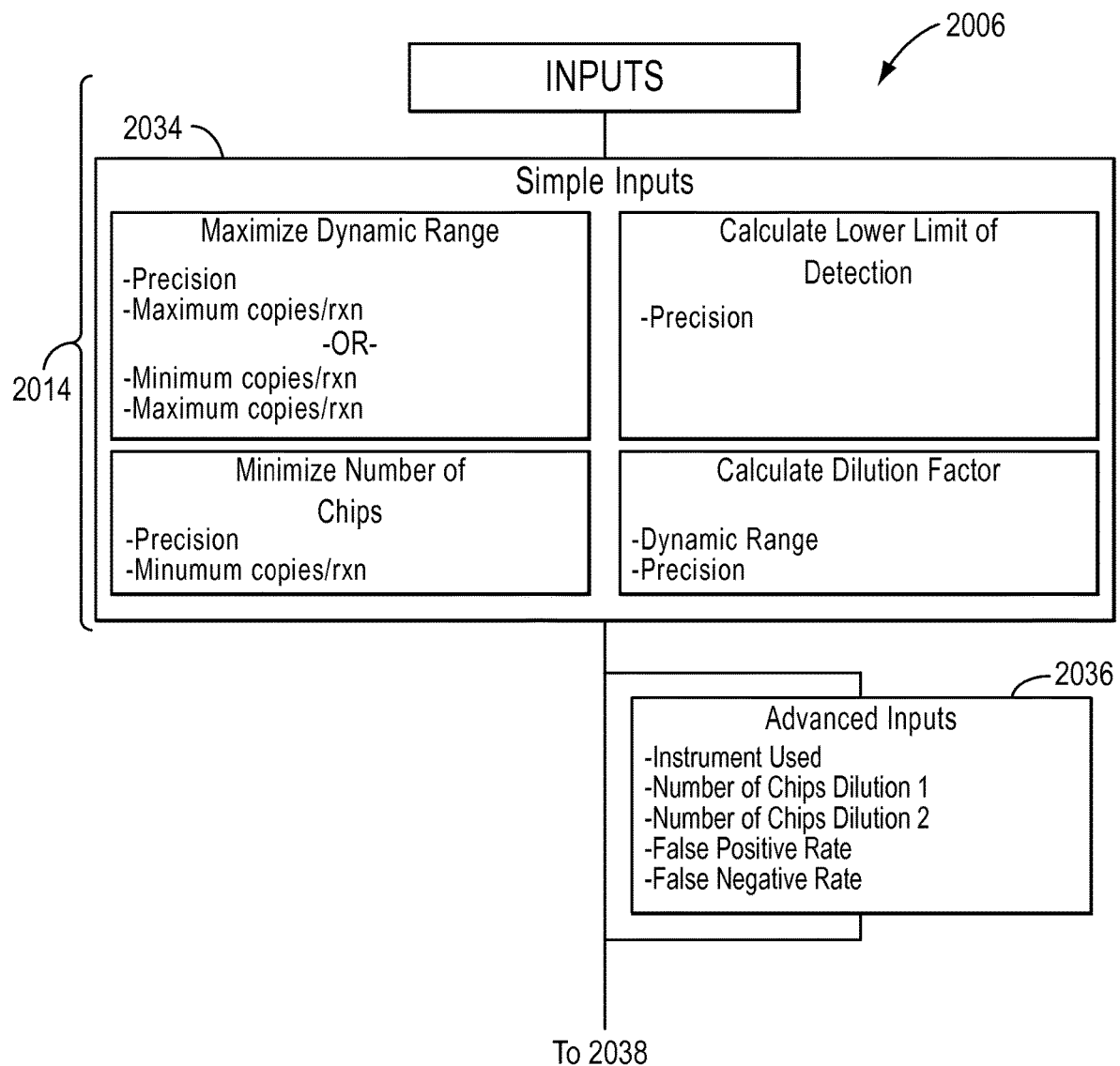
Figures 2B, 20B:
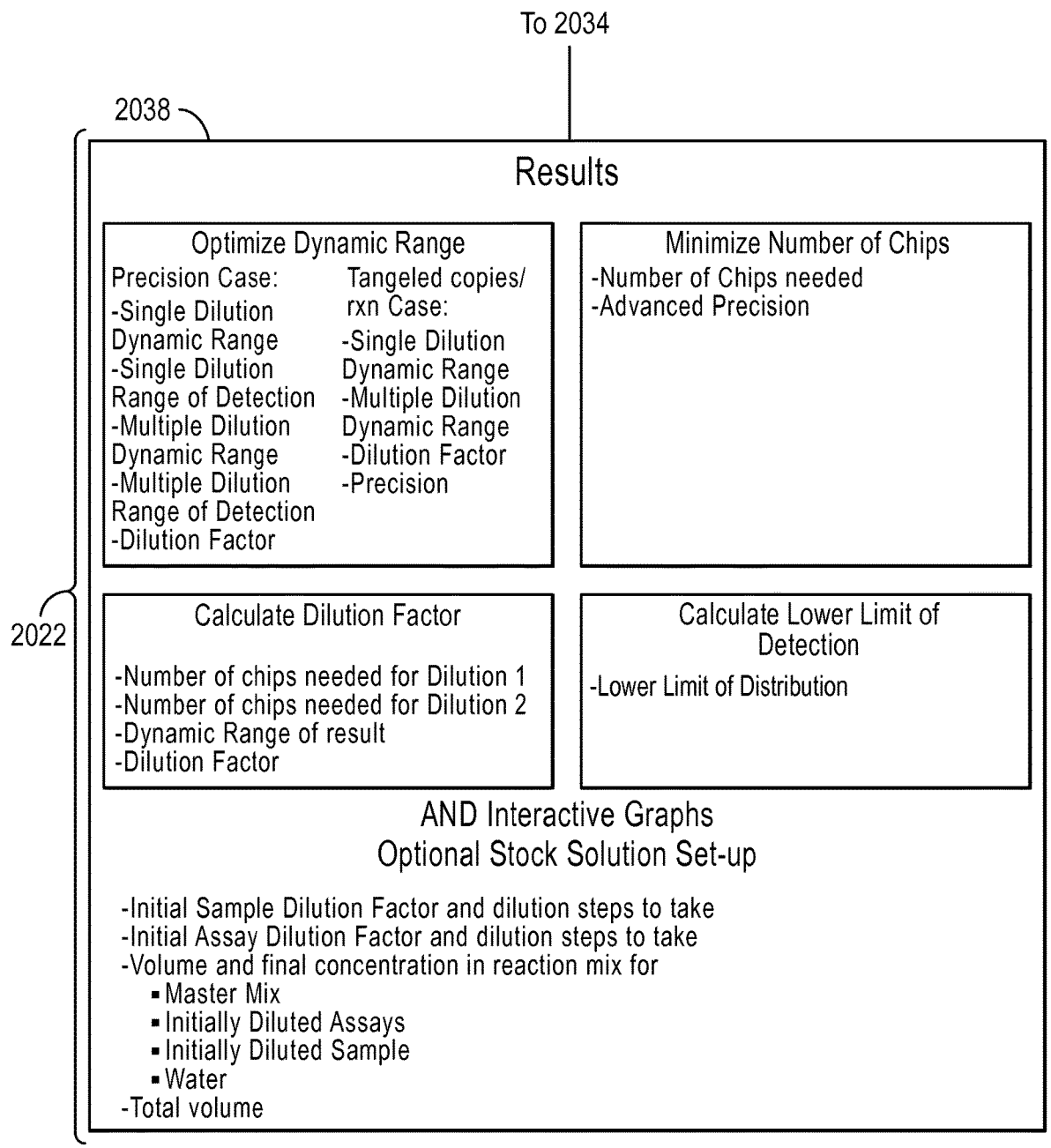
Figures 3, 20B:
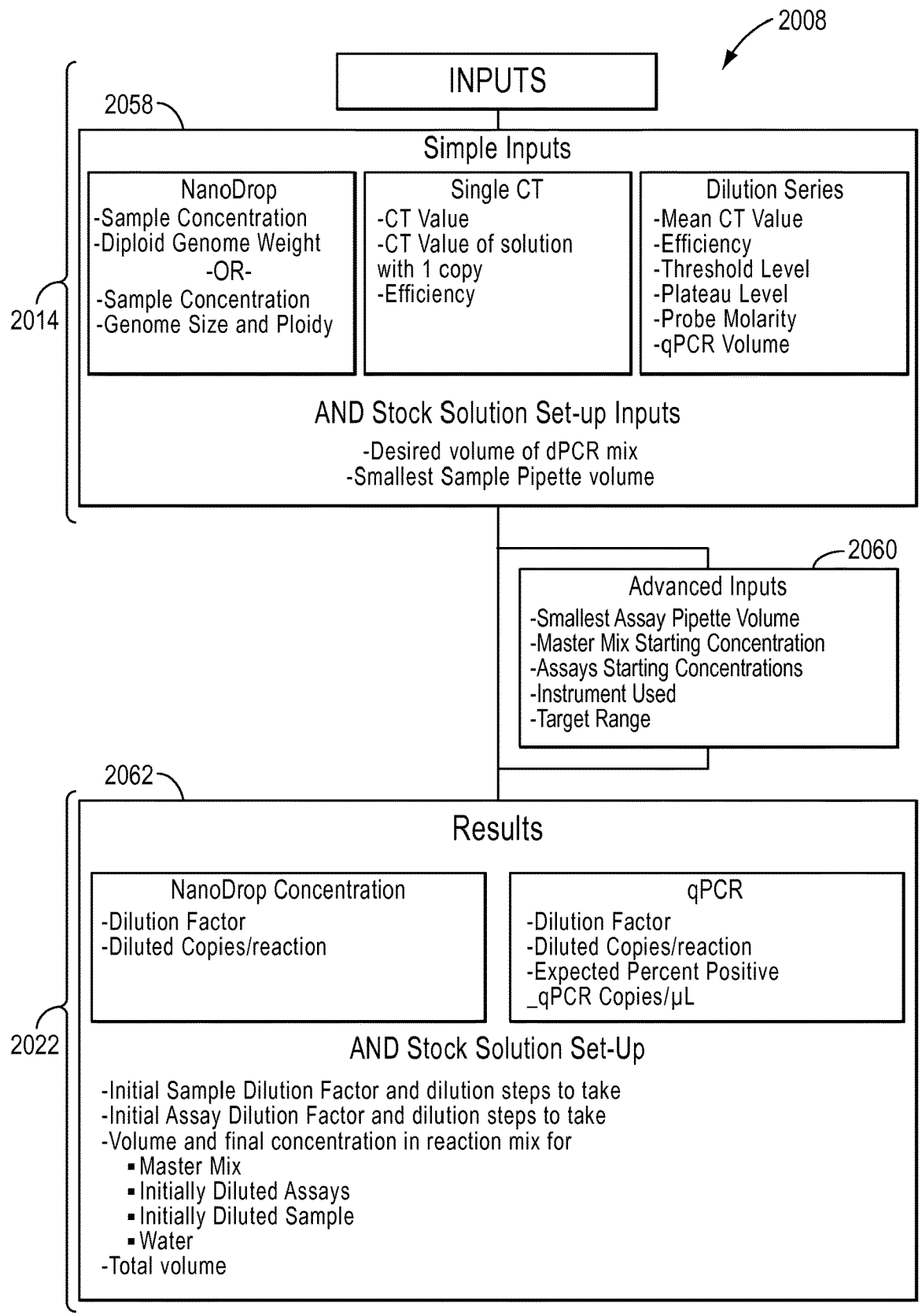
Figure 21B:
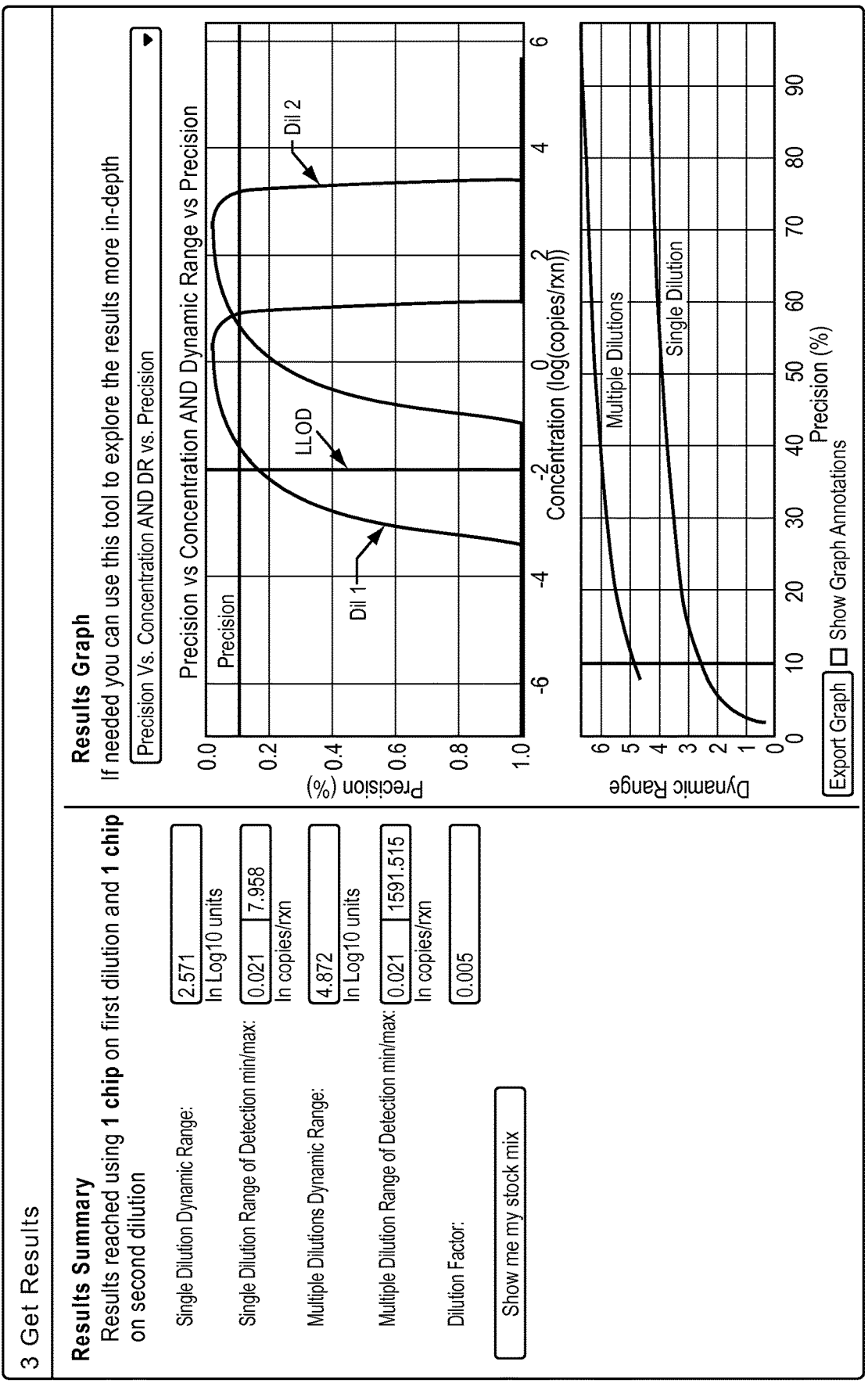
Figure 22C:
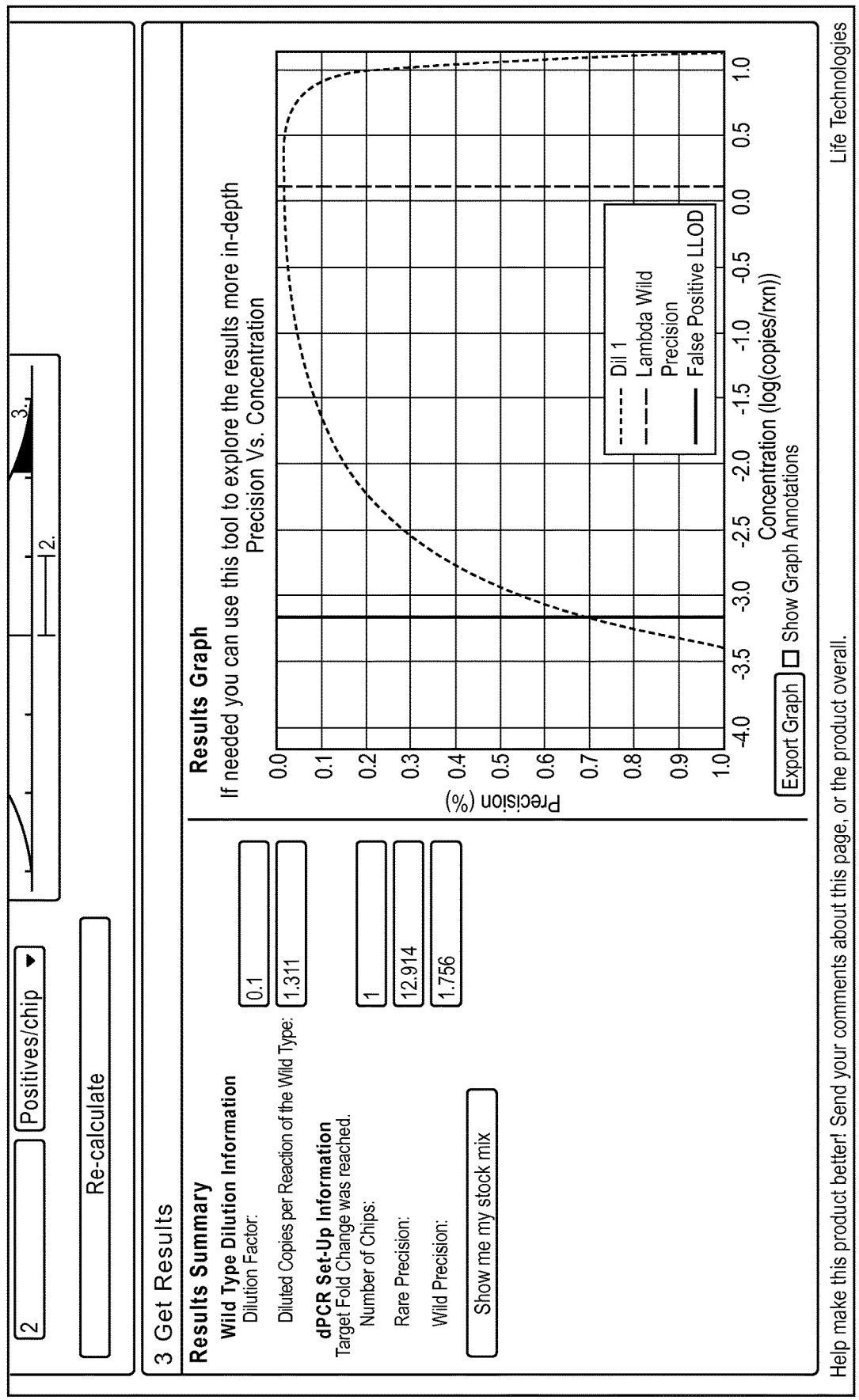

FIG. 20A and FIG. 20B illustrate flowchart 2000 examples of 3 different workflows supported by the digital PCR experiment designer tool according to various embodiments described herein. A workflow includes types of experiments a user may want to perform using dPCR. The dPCR experiment designer may help a user plan a desired experiment.

Workflows included in a dPCR experiment designer may include a rare mutation workflow 2004, an optimize detection attributes of a dPCR experiment for absolute quantification workflow 2006, and use of qPCR or NanoDrop data to estimate dilution factors for a dPCR experiment workflow 2008. According to various embodiments, the dPCR experiment designer allows a user to select the type of problem the user is trying to solve in step 2002. In other words, the user may select a workflow.

As an example, a user may select the rare mutation workflow 2004. The dPCR experiment designer may then lead the user to input the needed information to design an experiment. For example, in step 2010, the user will be asked to select the type of wild-type concentration they have. If the user has NanoDrop concentrations, the user will be asked to select the information about the genome that is known in step 2012, such as the diploid genome weight or the genome size and ploidy. If the user has qPCR readings as the source of wild-type concentration, the user will be queried to select whether the Ct values were derived with or without dilution series in step 2014.

Then, in step 2016, the user will be asked to select how they would like to constrain the lower limit of detection. The user may want to set the false positive distribution or set the lower limit of detection, for example.

The user may then input the needed information based on the NanoDrop concentration, single Ct, or dilution series used, for example, in step 2018. The user may also provide other advanced inputs in step 2020, such as the type of instrument used, the false positive rate, and the false negative rate.

Then, according to various embodiments, the user will be provided with results information in step 2024 including, but not limited to, wild type dilution information, dPCR set-up information, interactive graphs, and/or stock solution set up information. The user may then use this information to perform the desired rare mutation experiment.

FIG. 22A-22D illustrate a user interface displayed to a user implementing the rare mutation workflow 2004 of the dPCR experiment designer according to various embodiments described by the present teachings. FIGS. 22A-22D are described in more detail below.

In the optimize detection attributes of a dPCR experiment for absolute quantification workflow 2006, the user is asked to select the purpose of the experiment in step 2030. For example, the user may select maximize dynamic range, minimize the number of chips of reaction sites, calculate dilution factors, and/or calculate the lower limit of detection. If the user selects the purpose is to maximize dynamic range, the user is asked to select how they would like to constrain the dynamic range in step 2032. Depending on the purpose the user selects, the user inputs different information in step 2034. The user may also provide advanced inputs in step 2036, such as the type of instrument used, the number of chips (including a known number of reaction sites) used at a certain dilution, the false positive rate, and false negative rate. The results are provided to the user in step 2038.

FIG. 21A-21D illustrate a user interface of the dPCR experiment designer displayed to a user implementing optimize detection attributes workflow 2006 according to embodiments described by the present teachings. FIGS. 21A-21D are described in more detail below.

In the use qPCR or NanoDrop data to estimate the dilution factor for your digital experiment workflow 2008, the user will be asked to input the type of data they have in step 2050. For example, if the user has NanoDrop data, the user will be asked to input the type of diploid genome weight and the genome size and ploidy in step 2052. If the user has qPCR data, the user will be asked to select whether the Ct values derived was with or without dilution series in step 2054. Next, the user will be asked to select the type of experiment in step 2056. The types of experiments may be singleplex, duplex, SNP assay, or custom, for example. The user may be asked to input other information depending on the information selected in the previous queries in step 2058. Further, in step 2058, the user may also be asked to input parameters needed to determine stock-to-reaction mix dilution factors. In step 2060, the user may provide other advanced inputs. In step 2062, the user may be provided the results based on the type of data they used, qPCR or NanoDrop, for example.

FIG. 21A, FIG. 21B, FIG. 21C, and FIG. 21D illustrate an example of a method including steps for a gene expression quantification workflow using a dPCR experiment designer. The measurement precision requirement and the minimum copies/reaction inputs are used to estimate a dynamic range expansion dilution factor using the digital PCR model.

FIG. 22A, FIG. 22B, FIG. 22C, and FIG. 22D illustrate the steps of a rare mutation detection experiment design using the digital PCR experiment designer. In one example, a user can first run a qPCR experiment or a nanodrop reading to quantify the wild type target present in their sample. This information can be used by the dPCR experiment designer to estimate the target digital PCR dilution factor to enable detection of the background at a desired copies/reaction. Additionally, the dPCR experiment designer allows a user to input what they can experimentally determine about the false positive distribution for the assay and system. The user can then run non-target controls and determine a mean and standard deviation of the number of false positives typically seen in an experiment. This information, along with a target fold change and target p-value can allow the dPCR experiment designer to estimate the number of chips necessary to detect the rare event at the desired confidence level above background using the digital PCR model.

Quantification Results

This section demonstrates quantifying anywhere between 1 to 1e6 copies per μl on a dPCR system. In this example, the QuantStudio 3D from Life Technologies with a two chip two dilution strategy is used. In terms of the model, the requirements are 6 logs of dynamic range (DR), with a lowest limit of detection at 1 copy/μl. Using a 0.025% false positive rate and a 0.05% false negative rate, the dPCR experiment designer provides a recommendation of a dilution factor of 0.001.

Samples AA to GG, 6 logs apart, are at the concentrations given in the table below on the undiluted and diluted pairs of chips. The concentrations marked in the table below with double asterisk (**) were run on the system. Because this is a simulated example, the concentrations that would not be detectable by this system were not nm.

| Sample | Expected copies per μliter at conc | Expected copies per μliter at .001 dilution | Copies/Reaction from the actual runs |
| --- | --- | --- | --- |
| AA | 1000000 | 1000** | — |
| BB | 100000 | 100** | — |
| CC | 10000 | 10** | — |
| DD | 1000** | 1** | 1.4986 |
| EE | 100** | .1 | 0.1116 |
| FF | 10** | .01 | 0.0101 |
| GG | 1** | .001 | 0.0010 |

Figure 23A:
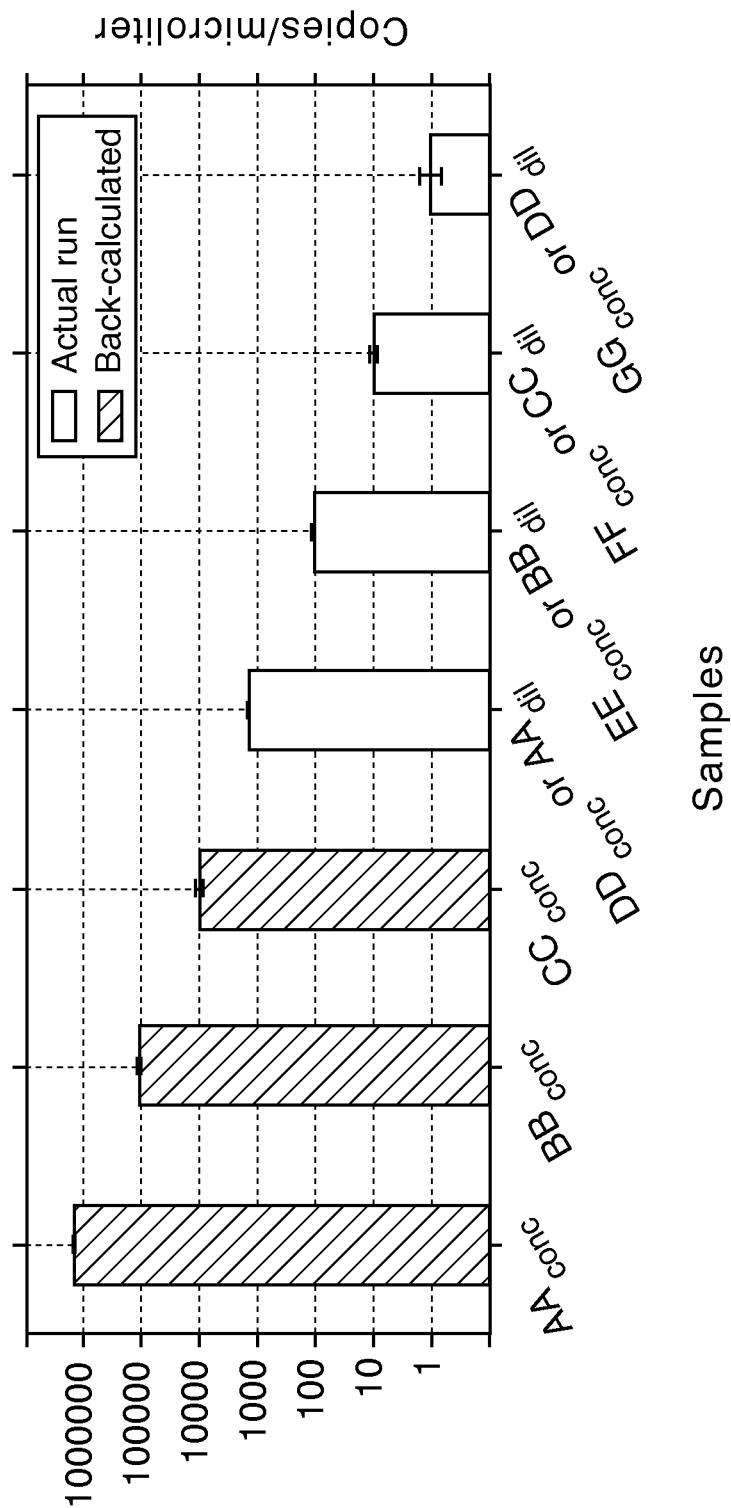
FIG. 23A and FIG. 23B illustrate quantification results of a dPCR experiment designer according to various embodiments described herein.
Figure 23B:
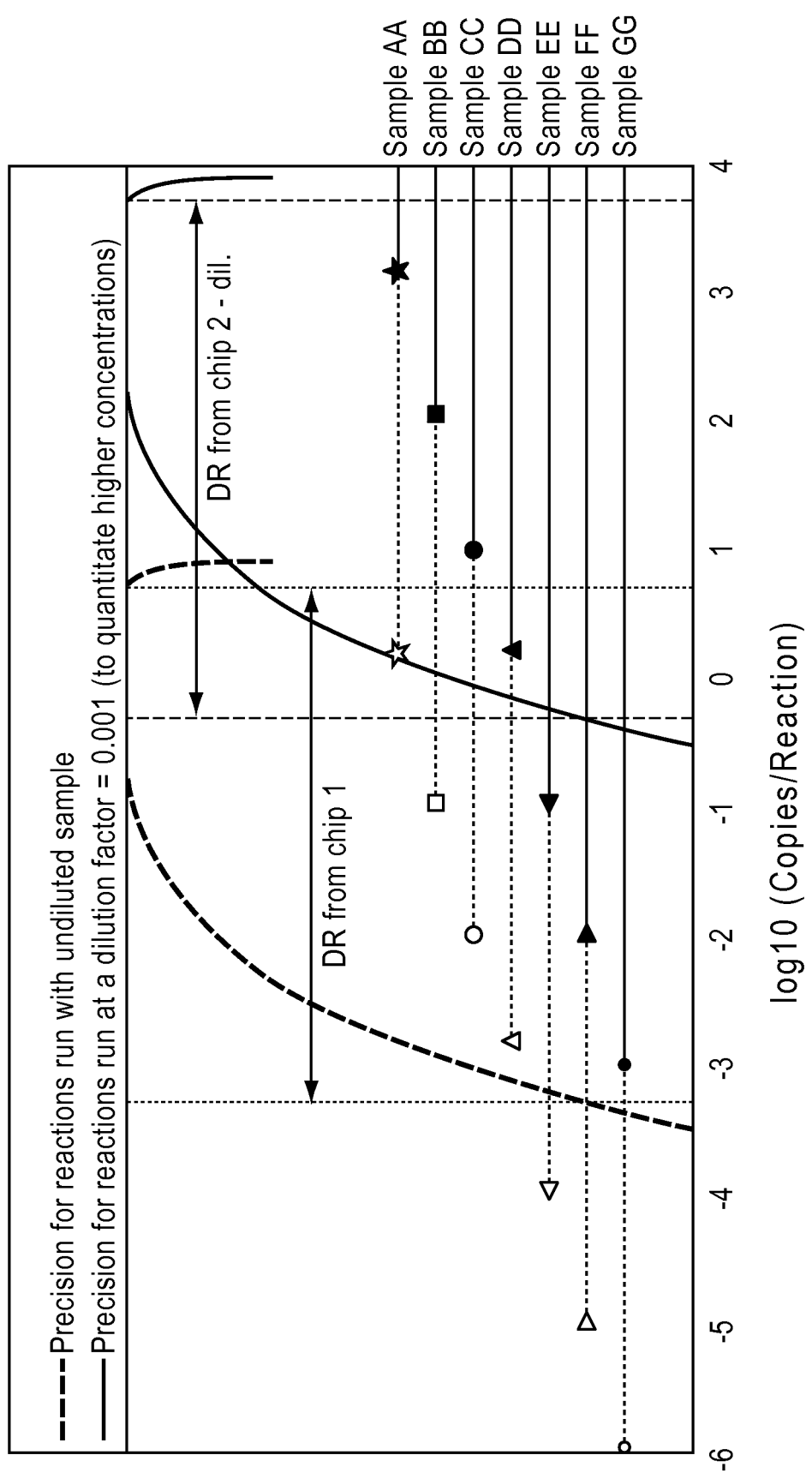

FIG. 23A illustrates the quantification results based on the model described above, according to embodiments described herein. Here, samples AA, BB and CC were accurately quantified on the dilute chip, while samples EE, FF and GG were accurately quantified on the undiluted chip. Sample DD was quantified using both data points. FIG. 23B projects the sample on the modeling schema used in the dPCR experiment designer according to various embodiments described herein.

Ratio Estimation Results

The following section demonstrates detecting rare targets against a background signal using computer simulated data with the two chip two dilution strategy. A 1:1000 ratio translates to 3 logs of dynamic range requirement. The lowest limit of detection was set at 10 copies per micro liter. System parameters for the model were chosen according to the Life Technologies QuantStudio 12K Flex. Using a 0.07% false positive rate and a 0.18% false negative rate, the system recommended a dilution factor of 0.005 for detecting at each target better than 30% precision.

Figure 24:
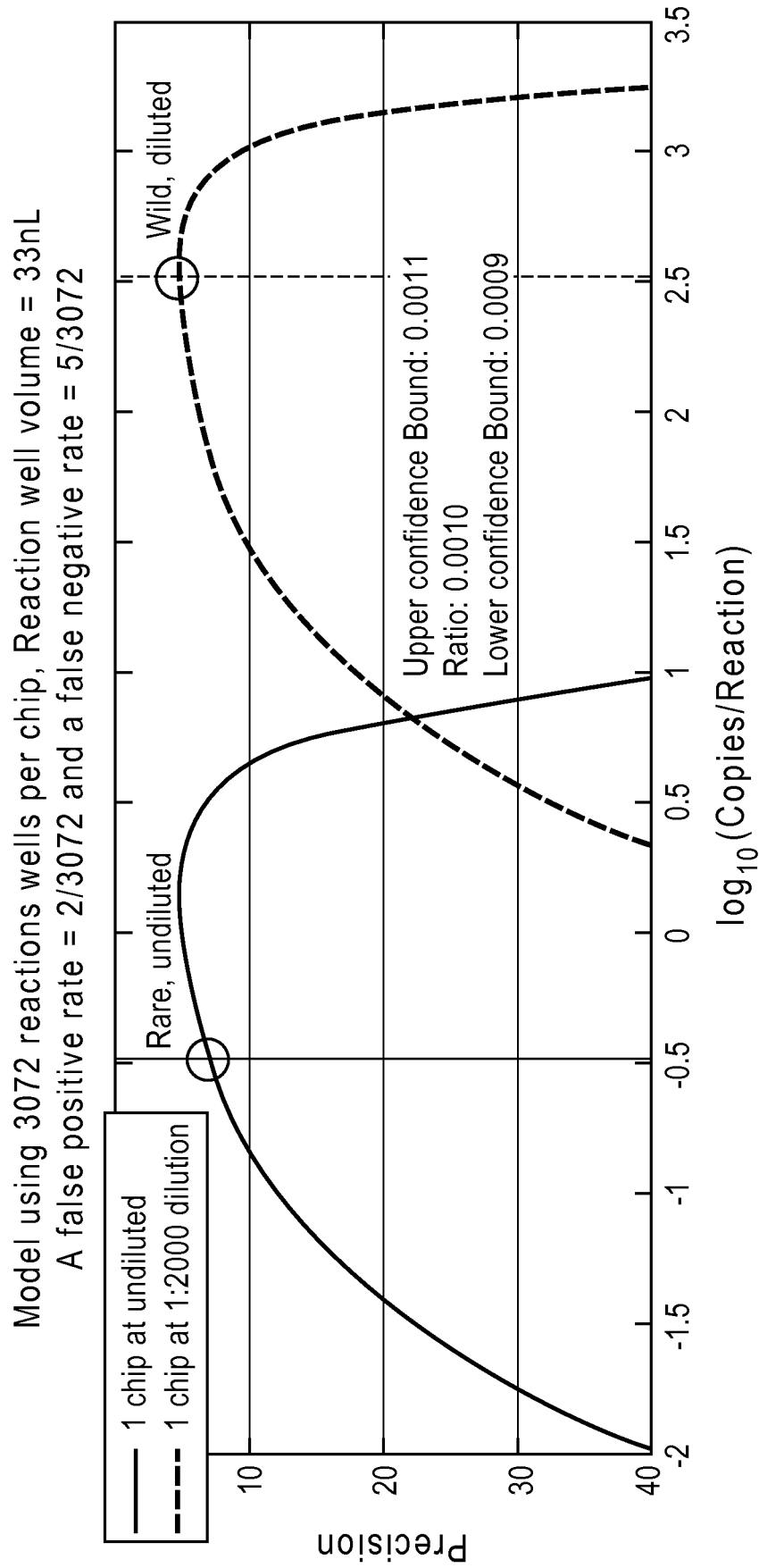
FIG. 24 illustrates rare target detection against a background signal according to various embodiments described herein.

FIG. 24 illustrates a model showing rare target estimation in the presence of 1000 fold background. Sample A was simulated with 10000 copies/μl of the abundant target and 10 copies/μl of the rare target. By sub-sampling from this data over a large number of iterations, at both the undiluted and the diluted configurations, the wild type was detected at the dilute point at 6.95% precision, while the rare target was detected at the undiluted point at 4.49% precision. The ratio was accurately predicted at 0.001.

Computer System

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on computer-readable media. Some other processes can be implemented using analog circuitry, as is well known to one of ordinary skill in the art. Additionally, memory or other storage, as well as communication components, may be employed in embodiments of the invention.

Figure 19:
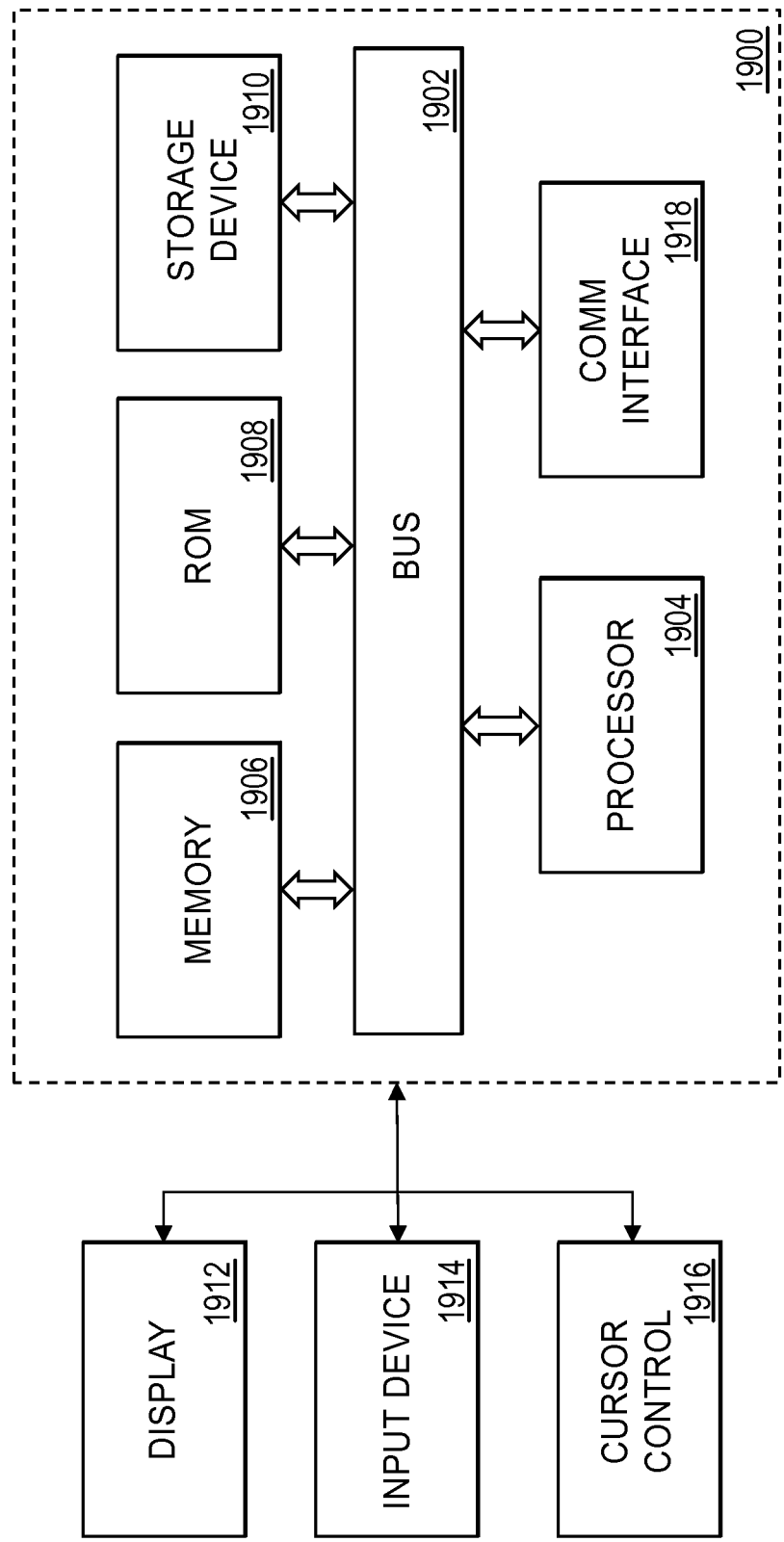
FIG. 19 illustrates an exemplary computing system that various embodiments described herein may be implemented.

FIG. 19 is a block diagram that illustrates a computer system 1900 that may be employed to carry out processing functionality, according to various embodiments of the dPCR experiment designer. Computing system 1900 can include one or more processors, such as a processor 1904. Processor 1904 can be implemented using a general or special purpose processing engine such as, for example, a microprocessor, controller or other control logic. In this example, processor 1904 is connected to a bus 1902 or other communication medium.

Further, it should be appreciated that a computing system 1900 of FIG. 19 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 1900 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art.

Computing system 1900 may include bus 1902 or other communication mechanism for communicating information, and processor 1904 coupled with bus 1902 for processing information.

Computing system 1900 also includes a memory 1906, which can be a random access memory (RAM) or other dynamic memory, coupled to bus 1902 for storing instructions to be executed by processor 1904. Memory 1906 also may be used for storing temporary variables or other intermediate information during execution of instructions to be executed by processor 1904. Computing system 1900 further includes a read only memory (ROM) 1908 or other static storage device coupled to bus 1902 for storing static information and instructions for processor 1904.

Computing system 1900 may also include a storage device 1910, such as a magnetic disk, optical disk, or solid state drive (SSD) is provided and coupled to bus 1902 for storing information and instructions. Storage device 1910 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 1910 may include other similar instrumentalities for allowing computer programs or other instructions or data to be loaded into computing system 1900. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 1910 to computing system 1900.

Computing system 1900 can also include a communications interface 1918. Communications interface 1918 can be used to allow software and data to be transferred between computing system 1900 and external devices. Examples of communications interface 1918 can include a modem, a network interface (such as an Ethernet or other NIC card), a communications port (such as for example, a USB port, a RS-232C serial port), a PCMCIA slot and card, Bluetooth, etc. Software and data transferred via communications interface 1918 are in the form of signals which can be electronic, electromagnetic, optical or other signals capable of being received by communications interface 1918. These signals may be transmitted and received by communications interface 1918 via a channel such as a wireless medium, wire or cable, fiber optics, or other communications medium. Some examples of a channel include a phone line, a cellular phone link, an RF link, a network interface, a local or wide area network, and other communications channels.

Computing system 1900 may be coupled via bus 1902 to a display 1912, such as a cathode ray tube (CRT) or liquid crystal display (LCD), for displaying information to a computer user. An input device 1914, including alphanumeric and other keys, is coupled to bus 1902 for communicating information and command selections to processor 1904, for example. An input device may also be a display, such as an LCD display, configured with touchscreen input capabilities. Another type of user input device is cursor control 1916, such as a mouse, a trackball or cursor direction keys for communicating direction information and command selections to processor 1904 and for controlling cursor movement on display 1912. This input device typically has two degrees of freedom in two axes, a first axis (e.g., x) and a second axis (e.g., y), that allows the device to specify positions in a plane. A computing system 1900 provides data processing and provides a level of confidence for such data. Consistent with certain implementations of embodiments of the present teachings, data processing and confidence values are provided by computing system 1900 in response to processor 1904 executing one or more sequences of one or more instructions contained in memory 1906. Such instructions may be read into memory 1906 from another computer-readable medium, such as storage device 1910. Execution of the sequences of instructions contained in memory 1906 causes processor 1904 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 1904 for execution. Such instructions, generally referred to as "computer program code" (which may be grouped in the form of computer programs or other groupings), when executed, enable the computing system 1900 to perform features or functions of embodiments of the present invention. These and other forms of computer-readable media may take many forms, including but not limited to, non-volatile media, volatile media, and transmission media. Non-volatile media includes, for example, solid state, optical or magnetic disks, such as storage device 1910. Volatile media includes dynamic memory, such as memory 1906. Transmission media includes coaxial cables, copper wire, and fiber optics, including the wires that comprise bus 1902.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 1904 for execution. For example, the instructions may initially be carried on magnetic disk of a remote computer. The remote computer can load the instructions into its dynamic memory and send the instructions over a telephone line using a modem. A modem local to computing system 1900 can receive the data on the telephone line and use an infra-red transmitter to convert the data to an infra-red signal. An infra-red detector coupled to bus 1902 can receive the data carried in the infra-red signal and place the data on bus 1902. Bus 1902 carries the data to memory 1906, from which processor 1904 retrieves and executes the instructions. The instructions received by memory 1906 may optionally be stored on storage device 1910 either before or after execution by processor 1904.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Although the present invention has been described with respect to certain exemplary embodiments, examples, and applications, it will be apparent to those skilled in the art that various modifications and changes may be made without departing from the invention.

What is claimed is:

1. A computer-implemented method of operating a biological analysis instrument, the method comprising:
receiving a first input of an optimization type for the dPCR experiment;
receiving a second input of at least one constraint related to a limit of detection by a dPCR system;
receiving a third input of a preset volume for each of a plurality of reaction sites;
receiving stock solution information to be used in the dPCR experiment;
generating a set of dPCR experiment design factors for the dPCR experiment by optimizing the dPCR experiment using a dPCR model, a stock-to reaction mix dilution factor, and the first, second, and third inputs, wherein the set of dPCR experiment design factors includes a number of reaction sites to be run in the biological analysis instrument;
displaying the set of dPCR experiment design factors; and
running the biological analysis instrument that has been set up using the dPCR experiment design factors to perform the dPCR experiment, wherein running the biological analysis instrument includes detecting an amplification signal from at least one reaction site.

2. The method of claim 1, wherein the optimization type is chosen from the following: maximizing dynamic range and minimizing a number of substrates, wherein each substrate includes a predetermined number of reaction sites, determining a dilution factor, and determining a lower limit of detection.

3. The method of claim 1, wherein generating the set of dPCR experiment design factors for the dPCR experiment includes calculating a minimum concentration of a target in each reaction site of the plurality of reaction sites.

4. A non-transitory computer-readable storage medium encoded with instructions for operating a biological analysis instrument, executable by a processor, the instructions comprising instructions for performing the method of claim 1.

5. The non-transitory computer-readable storage medium of claim 4, wherein the optimization type is chosen from the following: maximizing dynamic range and minimizing a number of substrates, wherein each substrate includes a predetermined number of reaction sites, determining a dilution factor, and determining a lower limit of detection.

6. The non-transitory computer-readable storage medium of claim 4, wherein generating the set of dPCR experiment design factors for the dPCR experiment includes calculating a minimum concentration of a target in each reaction site of the plurality of reaction sites.

7. A system for operating a biological analysis instrument, the system comprising:
a processor; and
a memory encoded with instructions executable by the processor, the instructions comprising instructions for:
receiving a first input of an optimization type for the dPCR experiment;
receiving a second input of at least one constraint related to a limit of detection by a dPCR system;
receiving a third input of a preset volume for each of a plurality of reaction sites;
receiving stock solution information to be used in the dPCR experiment;
generating a set of dPCR experiment design factors for the dPCR experiment by optimizing the dPCR experiment using a dPCR model, a stock-to reaction mix dilution factor, and the first, second, and third inputs, wherein the set of dPCR experiment design factors includes a number of reaction sites to be run in the biological analysis instrument;
displaying the set of dPCR experiment design factors; and
running the biological analysis instrument that has been set up using the dPCR experiment design factors to perform the dPCR experiment, wherein running the biological analysis instrument includes detecting an amplification signal from at least one reaction site.

8. The system of claim 7, wherein the optimization type is chosen from the following: maximizing dynamic range and minimizing a number of substrates, wherein each substrate includes a predetermined number of reaction sites, determining a dilution factor, and determining a lower limit of detection.

9. The system of claim 7, wherein generating the set of dPCR experiment design factors for the dPCR experiment comprises generating differing dilutions for at least two reaction sites of the plurality of reaction sites thereby increasing dynamic range of detectable concentrations.

10. The system of claim 7, wherein generating the set of dPCR experiment design factors for the dPCR experiment includes calculating a minimum concentration of a target in each reaction site of the plurality of reaction sites.

11. The method of claim 1, wherein generating the set of dPCR experiment design factors for the dPCR experiment comprises generating differing dilutions for at least two reaction sites of the plurality of reaction sites thereby increasing dynamic range of detectable concentrations.

12. The method of claim 1, wherein the at least one constraint comprises a precision measure.

13. The method of claim 1, wherein the first, second, and third inputs impact precision of the dPCR experiment.

14. The method of claim 1, wherein generating the dPCR experiment design factors is further based on system noise factors.

15. The non-transitory computer-readable storage medium of claim 4, wherein generating the set of dPCR experiment design factors for the dPCR experiment comprises generating differing dilutions for at least two reaction sites of the plurality of reaction sites thereby increasing dynamic range of detectable concentrations.

16. The non-transitory computer-readable storage medium of claim 4, wherein the at least one constraint comprises a precision measure.

17. The system of claim 7, wherein the at least one constraint comprises a precision measure.

18. A method for designing a digital PCR (dPCR) experiment for quantifying a concentration of a target within a sample using a plurality of reaction sites, the method comprising:
receiving, from a user, a selection of optimization type including one of: maximizing a dynamic range of detectable concentrations, minimizing the number of reaction sites needed for the dPCR experiment, calculating a dilution factor indicating a dilution of the sample, or calculating a lower limit of detection of the target;

receiving, from the user, a precision measure for the concentration of the target for an experiment;

determining a set of dPCR experiment design factors for the experiment based on the optimization type;

calculating values for the dPCR experiment design factors using the precision measure for the concentration;

displaying the calculated values of the set of dPCR experiment design factors to the user; and running the biological analysis instrument that has been set up using the set of dPCR experiment design factors to perform the experiment, wherein running the biological analysis instrument includes detecting an amplification signal from at least one reaction site.

19. A method for designing a digital PCR (dPCR) experiment for quantifying a concentration of a target using a plurality of reaction sites, the method comprising:

receiving, from a user, a selection of optimization type including: maximizing a dynamic range of detectable concentrations;

receiving, from the user, a minimum detectable concentration of the target in a reaction site for the experiment;

determining a set of dPCR experiment design factors for the experiment based on the optimization type wherein the set of dPCR experiment design factors includes a precision measure for the concentration of the target for the experiment;

calculating values for the design dPCR experiment factors using the minimum concentration of the target;

displaying the calculated values of the set of dPCR experiment design factors to the user; and running the biological analysis instrument that has been set up using the dPCR experiment design factors to perform the dPCR experiment, wherein running the biological analysis instrument includes detecting an amplification signal from at least one reaction site.

* * * * *